US012805577B2

(12) United States Patent
Courbat et al.

(10) Patent No.: US 12,805,577 B2
(45) Date of Patent: Nov. 24, 2026

(54) CARTRIDGE WITH RESONANT CIRCUIT FOR AN AEROSOL-GENERATING DEVICE

(71) Applicant: Philip Morris Products S.A., Neuchatel (CH)

(72) Inventors: Jerome Christian Courbat, Cortaillod (CH); David Murray Cross, Hertfordshire (GB); Vlad Revici, Manchester (GB)

(73) Assignee: Philip Morris Products S.A., Neuchatel (CH)

( * ) Notice: Subject to any disclaimer, the term of this patent is extended or adjusted under 35 U.S.C. 154(b) by 1020 days.

(21) Appl. No.: 17/906,436

(22) PCT Filed: Mar. 22, 2021

(86) PCT No.: PCT/EP2021/057294
§ 371 (c)(1),
(2) Date: Sep. 15, 2022

(87) PCT Pub. No.: WO2021/191156
PCT Pub. Date: Sep. 30, 2021

(65) Prior Publication Data
US 2023/0124313 A1 Apr. 20, 2023

(30) Foreign Application Priority Data
Mar. 23, 2020 (EP) .................................... 20165039

(51) Int. Cl.
*A24F 40/53* (2020.01)
*A24F 40/10* (2020.01)
(Continued)

(52) U.S. Cl.
CPC .............. *A24F 40/53* (2020.01); *A24F 40/10* (2020.01); *A24F 40/42* (2020.01); *A24F 40/46* (2020.01);
(Continued)

(58) Field of Classification Search
CPC .......... A24F 40/10; A24F 40/42; A24F 40/46; A24F 40/50; A24F 40/57; H05B 3/22; A61M 15/06
See application file for complete search history.

(56) References Cited

U.S. PATENT DOCUMENTS 6,796,508 B2 9/2004 Müller
7,646,305 B2 1/2010 Cote et al.
(Continued)

FOREIGN PATENT DOCUMENTS

CA 2 993 643 A1 2/2017
CN 110476478 A 11/2019
(Continued)

OTHER PUBLICATIONS

Extended European Search Report issued Oct. 13, 2022 in European Patent Application No. 20165039.7, 8 pages.
(Continued)

*Primary Examiner* — Brian W Jennison
(74) *Attorney, Agent, or Firm* — Oblon, McClelland, Maier & Neustadt, L.L.P.

(57) ABSTRACT

A cartridge for an aerosol-generating device is provided, the cartridge including: an aerosol-forming substrate; an electric heater configured to heat the aerosol-forming substrate; and a resonant circuit connected in parallel with the electric heater, the resonant circuit being configured to resonate at a predetermined resonant frequency, and the predetermined resonant frequency being associated with an identity of the cartridge. An aerosol-generating device and an aerosol generating system are also provided.

13 Claims, 9 Drawing Sheets

(51) Int. Cl.

| | |
|---|---|
| ***A24F 40/42*** | (2020.01) |
| ***A24F 40/46*** | (2020.01) |
| ***A24F 40/57*** | (2020.01) |
| ***A61M 15/06*** | (2006.01) |
| ***H05B 3/22*** | (2006.01) |

(52) U.S. Cl.

CPC ............... *A24F 40/57* (2020.01); *H05B 3/22* (2013.01); *A61M 15/06* (2013.01)

(56) References Cited

U.S. PATENT DOCUMENTS

| | | | | |
|---|---|---|---|---|
| 2003/0169153 | A1* | 9/2003 | Muller | G08B 13/2414 340/572.5 |
| 2017/0020191 | A1 | 1/2017 | Lamb et al. | |
| 2017/0055585 | A1* | 3/2017 | Fursa | A24F 40/46 |
| 2017/0231277 | A1 | 8/2017 | Mironov et al. | |
| 2019/0307170 | A1* | 10/2019 | Zarifian | G05D 11/13 |
| 2021/0145067 | A1 | 5/2021 | Bleloch et al. | |
| 2021/0186108 | A1* | 6/2021 | Korus | A24F 40/465 |

FOREIGN PATENT DOCUMENTS

| | | | |
|---|---|---|---|
| CN | 110876489 | A | 3/2020 |
| GB | 2529629 | A | 3/2016 |
| JP | 2009-516941 | A | 4/2009 |
| KZ | 33794 | B | 7/2019 |
| RU | 2 678 893 | C1 | 2/2019 |
| WO | WO 2013/098396 | A2 | 7/2013 |
| WO | WO 2018/195335 | A1 | 10/2018 |
| WO | WO 2019/228894 | A1 | 12/2019 |
| WO | WO 2020/020970 | A1 | 1/2020 |
| WO | WO 2020/043901 | A1 | 3/2020 |

OTHER PUBLICATIONS

International Search Report mailed on Jun. 28, 2021 in PCT/FR2020/051419 filed on Jul. 31, 2020 (4 pages).

International Search Report mailed on Jun. 28, 2021 in PCT/FR2020/051419 filed on Jul. 31, 2020 (9 pages).

Combined Russian Office Action and Search Report issued on Jul. 25, 2024 in Russian Patent Application No. 2022127071/03 (with English translation of Office Action), 14 pages.

Handbook of Elementary Mathematics, Mechanics and Physics, Eighth Edition, State Publishing House of the BSSR, Minsk, 1962, pp. 163-165.

Li Zhengping et al., Newly Compiled University Physics Experiments, China Petrochemical Press, Aug. 1998, p. 307.

Combined Chinese Office Action and Search Report issued on Oct. 17, 2025 in Chinese Patent Application No. 202180021395.1 (with English translation), 21 pages.

Malaysian Office Action and Search Report issued Dec. 15, 2025, in corresponding Malaysian Patent Application No. PI2022005048, 4 pages.

Combined Chinese Office Action and Search Report issued Apr. 30, 2025 in Chinese Patent Application No. 202180021395.1 (with English Translation), 19 pages.

Japanese Office Action issued Apr. 17, 2025 in Japanese Patent Application No. 2022-555808 (with English Translation), 11 pages.

Combined Chinese Office Action and Search Report issued Jan. 10, 2026, in corresponding Chinese Patent Application No. 202180021395.1 (with English Translation), 23 pages.

Bai Hui et al., "Development and Innovation of Foreign Tobacco Enterprises", Huazhong University of Science and Technology Press, Dec. 31, 2019, 4 pages.

* cited by examiner

CARTRIDGE WITH RESONANT CIRCUIT FOR AN AEROSOL-GENERATING DEVICE

The present disclosure relates to a cartridge for an aerosol-generating device. In particular, the present disclosure relates to a cartridge for an aerosol-generating device in which the cartridge comprises a resonant circuit which can be used to identify the cartridge or its contents. The present disclosure also relates to an aerosol-generating device for use with the cartridge and an aerosol-generating system comprising both the cartridge and the device.

Handheld electrically operated aerosol-generating systems can have a modular construction comprising a device and a removable cartridge. In known aerosol-generating systems the device typically comprises a battery and control electronics and the cartridge comprises a liquid storage portion holding a supply of liquid aerosol-forming substrate and an electric heater. The heater typically comprises a coil of wire which is wound around an elongate wick which transfers liquid aerosol-forming substrate from the liquid storage portion to the heater. An electric current can be passed through the coil of wire to heat the heater and thereby generate an aerosol from the aerosol-forming substrate. The cartridge generally also comprises a mouthpiece through which a user may draw aerosol into their mouth.

Cartridges are typically interchangeable and can comprises a range of different aerosol-forming substrates which may vary considerably in composition, flavour, strength or other characteristics. A user is able to interchange cartridges at will. However, the conditions required to aerosolise a certain aerosol-forming substrate or produce a certain user experience may vary from cartridge to cartridge. In particular, the heating profile required for a particular cartridge may depend on the characteristics of the aerosol-forming substrate.

It would therefore be desirable to provide a means of automatically identifying a cartridge so that an aerosol-generating device can adapt its aerosolisation conditions accordingly.

According to an example of the present disclosure, there is provided a cartridge for an aerosol-generating device. The cartridge may comprise an aerosol-forming substrate. The cartridge may comprise an electric heater for heating the aerosol-forming substrate. The cartridge may comprise a resonant circuit. The resonant circuit may be configured to resonate at a predetermined resonant frequency. The predetermined resonant frequency may be associated with an identity of the cartridge.

As used herein, the term "resonant circuit" refers to an electrical circuit that exhibits resonance or resonant behaviour. That is, the circuit naturally oscillates with greater amplitude at a certain frequency, called its resonant frequency, than at other frequencies.

Advantageously, by configuring the resonant circuit to resonate at a predetermined resonant frequency, an aerosol-generating device is able to clearly identify a cartridge, or the aerosol-forming substrate contained in the cartridge, by determining the frequency at which resonance occurs. In other words, the resonant frequency acts as a characteristic feature of the cartridge. Different predetermined resonant frequencies can be used for different cartridges to allow different cartridges to be discriminated. Once a cartridge has been identified, the aerosol-generating device can then apply an appropriate heating profile for the aerosol-forming substrate contained in the cartridge.

Advantageously, the resonant circuit can be constructed from relatively few inexpensive electrical components and therefore the resonant circuit represents a simply and cost effective way of identifying a cartridge compared to other identification methods such as memory chips or RFID tags.

A further advantage of using a resonant circuit to identify a cartridge is that the resonant circuit can be used as an anti-counterfeiting measure. If a user tried to connect an unauthorised cartridge to their aerosol-generating device which did not have a resonant circuit, or if a resonant circuit was used which did not have an expected predetermined resonant frequency, the aerosol-generating device may be able to identify the cartridge as unauthorised, or as a possible counterfeit, and either alert the user or block operation of the device.

The resonant circuit may be connected in parallel with the electric heater. An advantage of connecting the resonant circuit in parallel with the electric heater is that it assists in reducing energy losses in the resonant circuit during heating by avoiding connecting passive electrical components of the resonant circuit in series with the heater. It is desirable to minimise energy consumption by the resonant circuit during heating so that more energy can be supplied to the heater. If passive components were arranged in series with the heater, then current supplied to the heater would also pass through these components resulting in energy losses in these components, for example, in the parasitic elements, of these components, such as parasitic resistances.

A further advantage of connecting the resonant circuit in parallel with the electric heater is that the cartridge requires only two electrical contacts both to supply power to the heater and also to provide an input signal to, and receive an output signal from, the resonant circuit. If the resonant circuit were connected in series at least one extra connection would be required to receive an output signal from the resonant circuit.

The resonant circuit may comprise three components or less. The resonant circuit may comprise two components or less. This reduces the complexity and cost of the circuit and also reduces the size of the circuit, that is, the circuit requires less printed circuit board area.

The resonant circuit may comprise a capacitor and an inductor. This is the simplest type of resonant circuit and can be implemented with just two passive components. Advantageously, where the resonant circuit is arranged in parallel with the heater and a direct current (DC) voltage is applied to the cartridge to heat the heater, the capacitor blocks DC voltage and effectively acts as an open-circuit so that no direct current flows through the resonant circuit. Instead, direct current flows solely through the heater and therefore energy losses in the resonant circuit are minimised during heating.

For a resonant circuit comprising an inductor and a capacitor (a so-called LC circuit), resonance occurs when the circuit receives, or is driven by, an input alternating signal which is alternating or oscillating at the resonant frequency. The resonant frequency is the frequency at which the inductive and capacitive reactances are equal in magnitude. The resonant frequency of the resonant circuit can be determined by Equation (1):

$$f_0 = \frac{1}{2\pi\sqrt{LC}} \tag{1}$$

where $f_0$ is the resonant frequency, L is the inductance of the inductor and C is the capacitance of the capacitor.

The capacitor and inductor may be connected in series. The series arrangement of the capacitor and inductor may be connected in parallel across the heater. In a series LC circuit, resonance occurs when the capacitive reactance and the inductive reactance are equal in magnitude but opposite in phase such that the two reactances cancel each other. Therefore, when the series arrangement of the capacitor and inductor is resonating, the impedance of the resonant circuit is at a minimum.

As mentioned above, where the resonant circuit is arranged in parallel with the heater and a direct current (DC) voltage is applied to the cartridge to heat the heater, the capacitor blocks DC voltage and effectively acts as an open-circuit so that no direct current flows through the resonant circuit. Therefore, by connecting the inductor in series with the capacitor, DC current is also prevented from flowing through the inductor, thereby reducing energy losses.

The predetermined resonant frequency of the resonant circuit may be determined by the capacitance of the capacitor. In this situation, the inductance of the inductor may be fixed. The inductance of the inductor may be fixed at approximately 1 microhenry (μH), although any suitable inductance value may be used to achieve the predetermined resonant frequency. The predetermined resonant frequency may be changed by changing the capacitance of the capacitor. The capacitance of the capacitor may be changed by using capacitors having different capacitance values. Advantageously, this merely involves changing a single component for a particular resonant circuit. Any capacitor having a suitable capacitance value for achieving the predetermined resonant frequency may be used. The capacitance of the capacitor may be in the range 0.1 nanofarads (nF) to 10 nF. The capacitance of the capacitor may be varied by using a range of standard capacitor values. For example, the following capacitor values may be used: 0.27 nF, 0.39 nF, 0.56 nF, 0.82 nF, 1.2 nF, 1.8 nF, 2.7 nF, 3.9 nF, 5.6 nF, and 8.2 nF. These values are taken from the E12 series of standard capacitor values and are therefore readily available.

Alternatively, the predetermined resonant frequency of the resonant circuit may be determined by the inductance of the inductor. The resonant frequency may be changed by changing the inductance of the inductor. In this situation, the capacitance of the capacitor may be fixed. The capacitance of the capacitor may be fixed at 270 nanofarads, although any suitable capacitance value may be used to achieve the predetermined resonant frequency. The inductance of the inductor may be varied by using inductors having different inductance values. Advantageously, this merely involves changing a single component for a particular resonant circuit. Any inductor having a suitable inductance value for achieving the predetermined resonant frequency may be used. The inductance of the inductor may be in the range 0.1 nanohenries (nH) to 330 nH. For example, the following inductor values may be used: 1 nH, 1.5 nH, 2.2 nH, 3.3 nH, 4.7 nH, 6.8 nH, 10 nH, 15 nH, 22 nH, and 33 nH. These values are taken from the E12 series of standard inductor values and are therefore readily available.

Alternatively, the predetermined resonant frequency of the resonant circuit may be determined by both the capacitance of the capacitor and the inductance of the inductor. Any suitable combination of capacitance and inductance values may be used to achieve the predetermined resonant frequency.

The predetermined resonant frequency may be in the range 10 kilohertz (kHz) to 100 megahertz (MHz), preferably in the range 100 kHz to 20 MHz, and more preferably in the range 1 MHz to 11 MHz. An advantage of using relatively high resonant frequencies, for example frequencies in the megahertz range, is that it reduces the measurement time required to detect resonance. The inventors have found that a frequency sweep of high frequencies can be performed more quickly than a frequency sweep of low frequencies. A further advantage of using frequencies in the MHz range is that it increases the proportion of the measurement signal that passes through the resonant circuit compared to the heater. When an alternating signal is input to the cartridge to detect resonance, it splits between the heater and the resonant circuit. In contrast to a DC signal, an alternating signal is able to pass through the capacitor of the resonant circuit. It has been found that a smaller proportion of the signal flows through the heater at higher frequencies than at lower frequencies. Advantageously, this makes detection of the resonant frequency easier compared to using lower frequencies and also reduces energy losses in the heater.

The resonant circuit may comprise a plurality of capacitors arranged in parallel. The combined capacitance of the plurality of capacitors may be used to produce resonance. The inventors have found that implementing the capacitive part of the resonant circuit using two or more capacitors arranged in parallel assists in improving the frequency response of the resonant circuit. That is, the parallel arrangement helps to improve the signal output from the resonant circuit for a particular input frequency which assists in detection of the resonant frequency. This is because the parallel arrangement of capacitors helps to reduce parasitic series resistances.

The resonant circuit may be arranged on a printed circuit-board (PCB). The resonant circuit may be arranged on its own separate PCB. This allows the resonant circuit to be manufactured as a separate modular part of the cartridge and act as a standalone identification or anti-counterfeiting device. Given that the resonant circuit can be implemented using relatively few components, less PCB area is required such that the PCB can easily fit within the cartridge of a handheld aerosol-generating device.

The inductor may be formed directly on the PCB as a conductive track. This can be fabricated easily during PCB manufacture and reduces the number of components required for the resonant circuit. Alternatively, the inductor may comprise a discrete surface mounted device mounted on the PCB. The capacitor may also comprise a discrete surface mounted device mounted on the PCB.

The resonant circuit may comprise a capacitor connected in parallel with the heater. The resonant circuit may be configured to use a parasitic inductance of the resonant circuit in combination with the capacitance of the capacitor to produce resonance.

As used herein, the term “parasitic inductance” refers to an inevitable inductance effect of all “real” electronic components which can result from a number of factors such as the geometry of the component, the materials of the component or how the component is used in a circuit. For example, in addition to a resistance, a resistor may have a parasitic inductance and in addition to a capacitance, a capacitor may have a parasitic inductance. The term “real” above is used to distinguish actual physical components used in circuits from ideal components which exist purely in theory and have a single intended characteristic such as a pure resistance or a pure capacitance with no parasitic element. Generally, parasitic inductance is an unwanted inductance effect. Furthermore, its effect is often insignificant and in many applications it can be ignored. However, the inventors have surprisingly found that in certain applications it can be a benefit.

Advantageously, by using a parasitic inductance of the resonant circuit instead of an actual inductor component, the number of components in the resonant circuit can be reduced. This simplifies the circuit and reduces the PCB area required for the circuit.

Since parasitic inductances are often relatively small compared to the inductance of actual inductor components, the resonant frequencies they produce are generally higher. The predetermined resonant frequency may be in the range 100 kHz to 100 MHz and preferably in the range 1 MHz to 50 MHz. These frequency ranges have the same advantages discussed above when describing a resonant circuit using an actual inductor.

The predetermined resonant frequency of the resonant circuit may be determined by the capacitance of the capacitor. The predetermined resonant frequency of the resonant circuit may be changed by changing the capacitance of the capacitor. This can be achieved by using capacitors having different capacitance values and merely involves changing a single component for a particular resonant circuit. Any capacitor having a suitable capacitance value for achieving the predetermined resonant frequency may be used. The capacitance of the capacitor may be in the range 1 nanofarads (nF) to 100 nF. The capacitance of the capacitor may be varied by using a range of standard capacitor values. For example, the following capacitor values may be used: 2.7 nF, 3.9 nF, 5.6 nF, 8.2 nF, 12 nF, 18 nF, 27 nF, 39 nF, 56 nF, and 82 nF. These values are taken from the E12 series of standard capacitor values and are therefore readily available.

The resonant circuit may be arranged to be connected to an alternating signal source and is configured to resonate when the predetermined resonant frequency substantially equals the frequency of the alternating signal. This allows the resonant circuit to receive, or be driven by, an input alternating signal to determine the resonant frequency.

The heater may comprise one or more heating elements. The heating element may have any suitable shape or geometry. For example, the heating element may be straight, formed as a coil or have an undulating or meandering shape. The heating element may comprise a heating wire or filament, for example a Ni—Cr (Nickel-Chromium), platinum, tungsten or alloy wire.

The heating element may be formed from any material with suitable electrical properties. Suitable materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, constantan, nickel-, cobalt-, chromium-, aluminum-, titanium-, zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminum based alloys and iron-manganese-aluminum based alloys. Timetal® is a registered trade mark of Titanium Metals Corporation. The filaments may be coated with one or more insulators. Preferred materials for the electrically conductive filaments are stainless steel and graphite, more preferably 300 series stainless steel like AISI 304, 316, 304L, 316L. Additionally, the electrically conductive heating element may comprise combinations of the above materials. A combination of materials may be used to improve the control of the resistance of the substantially flat heating element. For example, materials with a high intrinsic resistance may be combined with materials with a low intrinsic resistance. This may be advantageous if one of the materials is more beneficial from other perspectives, for example price, machinability or other physical and chemical parameters. Advantageously, high resistivity heaters allow more efficient use of battery energy.

The heating element may be a fluid-permeable heating element. The fluid permeable heating element may comprise a plurality of interstices or apertures extending from a first side to a second side of the heating element and through which fluid may pass.

The heating element may comprise a substantially flat heating element to allow for simple manufacture. Geometrically, the term "substantially flat" heating element is used to refer to a heating element that is in the form of a substantially two dimensional topological manifold. Thus, the substantially flat heating element extends in two dimensions along a surface substantially more than in a third dimension. In particular, the dimensions of the substantially flat heating element in the two dimensions within the surface is at least five times larger than in the third dimension, normal to the surface. An example of a substantially flat heating element is a structure between two substantially imaginary parallel surfaces, wherein the distance between these two imaginary surfaces is substantially smaller than the extension within the surfaces. In some embodiments, the substantially flat heating element is planar. In other embodiments, the substantially flat heating element is curved along one or more dimensions, for example forming a dome shape or bridge shape.

The heating element may comprise a plurality of electrically conductive filaments. The term "filament" is used to refer to an electrical path arranged between two electrical contacts. A filament may arbitrarily branch off and diverge into several paths or filaments, respectively, or may converge from several electrical paths into one path. A filament may have a round, square, flat or any other form of cross-section. A filament may be arranged in a straight or curved manner.

The heating element may be an array of filaments, for example arranged parallel to each other. Preferably, the filaments may form a mesh. The mesh may be woven or non-woven. The mesh may be formed using different types of weave or lattice structures. Alternatively, the electrically conductive heating element consists of an array of filaments or a fabric of filaments. The mesh, array or fabric of electrically conductive filaments may also be characterized by its ability to retain liquid.

In a preferred example, a substantially flat heating element may be constructed from a wire that is formed into a wire mesh. Preferably, the mesh has a plain weave design. Preferably, the heating element is a wire grill made from a mesh strip.

The electrically conductive filaments may define interstices between the filaments and the interstices may have a width of between 10 micrometres and 100 micrometres. Preferably, the filaments give rise to capillary action in the interstices, so that in use, liquid to be vaporized is drawn into the interstices, increasing the contact area between the heating element and the liquid aerosol-forming substrate.

The electrically conductive filaments may form a mesh of size between 60 and 240 filaments per centimetre (+/−10 percent). Preferably, the mesh density is between 100 and 140 filaments per centimetres (+/−10 percent). More preferably, the mesh density is approximately 115 filaments per centimetre. The width of the interstices may be between 100 micrometres and 25 micrometres, preferably between 80 micrometres and 70 micrometres, more preferably approximately 74 micrometres. The percentage of open area of the mesh, which is the ratio of the area of the interstices to the total area of the mesh may be between 40 percent and 90 percent, preferably between 85 percent and 80 percent, more preferably approximately 82 percent.

The electrically conductive filaments may have a diameter of between 8 micrometres and 100 micrometres, preferably between 10 micrometres and 50 micrometres, more preferably between 12 micrometres and 25 micrometres, and most preferably approximately 16 micrometres. The filaments may have a round cross section or may have a flattened cross-section.

The area of the mesh, array or fabric of electrically conductive filaments may be small, for example less than or equal to 50 square millimetres, preferably less than or equal to 25 square millimetres, more preferably approximately 15 square millimetres. The size is chosen such to incorporate the heating element into a handheld system. Sizing of the mesh, array or fabric of electrically conductive filaments less or equal than 50 square millimetres reduces the amount of total power required to heat the mesh, array or fabric of electrically conductive filaments while still ensuring sufficient contact of the mesh, array or fabric of electrically conductive filaments to the liquid aerosol-forming substrate. The mesh, array or fabric of electrically conductive filaments may, for example, be rectangular and have a length between 2 millimetres to 10 millimetres and a width between 2 millimetres and 10 millimetres. Preferably, the mesh has dimensions of approximately 5 millimetres by 3 millimetres.

Preferably, the filaments are made of wire. More preferably, the wire is made of metal, most preferably made of stainless steel.

The electrical resistance of the mesh, array or fabric of electrically conductive filaments of the heating element may be between 0.3 Ohms and 4 Ohms. Preferably, the electrical resistance is equal or greater than 0.5 Ohms. More preferably, the electrical resistance of the mesh, array or fabric of electrically conductive filaments is between 0.6 Ohms and 0.8 Ohms, and most preferably about 0.68 Ohms. The electrical resistivity of the mesh, array or fabric of electrically conductive filaments is preferably at least an order of magnitude, and more preferably at least two orders of magnitude, greater than the electrical resistivity of any electrically conductive contact portions. This ensures that the heat generated by passing current through the heating element is localized to the mesh or array of electrically conductive filaments. It is advantageous to have a low overall resistance for the heating element if the system is powered by a battery. A low resistance, high current system allows for the delivery of high power to the heating element. This allows the heating element to heat the electrically conductive filaments to a desired temperature quickly.

Alternatively, the heating element may comprise a heating plate in which an array of apertures is formed. The apertures may be formed by etching or machining, for example. The plate may be formed from any material with suitable electrical properties, such as the materials described above in relation to the heating element.

Electrical contact portions may be positioned on opposite ends of the heating element. The electrical contact portions may comprise two electrically conductive contact pads. The electrically conductive contact pads may be positioned at an edge area of the heating element. Preferably, the at least two electrically conductive contact pads may be positioned on extremities of the heating element. An electrically conductive contact pad may be fixed directly to electrically conductive filaments of the heating element. An electrically conductive contact pad may comprise a tin patch. Alternatively, an electrically conductive contact pad may be integral with the heating element.

The cartridge may comprise a liquid storage compartment. Liquid aerosol-forming substrate is held in the liquid storage compartment. The liquid storage compartment may have first and second portions in communication with one another. A first portion of the liquid storage compartment may be on an opposite side of the heater to the second portion of the liquid storage compartment. Liquid aerosol-forming substrate is held in the first portion of the liquid storage compartment.

Advantageously, the first portion of the storage compartment is larger than the second portion of the storage compartment. The cartridge may be configured to allow a user to draw or suck on the cartridge to inhale aerosol generated in the cartridge. In use a mouth end opening of the cartridge is typically positioned above the heater, with the first portion of the storage compartment positioned between the mouth end opening and the heater. Having the first portion of the storage compartment larger than the second portion of the storage compartment ensures that liquid is delivered from the first portion of the storage compartment to the second portion of the storage compartment, and so to the heater, during use, under the influence of gravity.

The cartridge may have a mouth end through which generated aerosol can be drawn by a user and a connection end configured to connect to an aerosol-generating device, wherein a first side of the heater faces the mouth end and a second side of the heater faces the connection end.

The cartridge may define an enclosed airflow path or passage from an air inlet past the first side of the heater to a mouth end opening of the cartridge. The enclosed airflow passage may pass through the first or second portion of the liquid storage compartment. In one embodiment the air flow path extends between the first and second portions of the liquid storage compartment. Additionally, the air flow passage may extend through the first portion of the liquid storage compartment. For example, the first portion of the liquid storage compartment may have an annular cross section, with the air flow passage extending from the heater to the mouth end portion through the first portion of the liquid storage compartment. Alternatively, the air flow passage may extend from the heater to the mouth end opening adjacent to the first portion of the liquid storage compartment.

The cartridge may comprise a capillary material in contact with the second side of the heater. The capillary material delivers liquid aerosol-forming substrate to the heater against the force of gravity. By requiring the liquid aerosol forming substrate to be move against the force of gravity in use to reach the heater, the possibility of large droplets of the liquid entering the airflow passage is reduced.

A capillary material is a material that liquid from one end of the material to another by means of capillary action. The capillary material may have a fibrous or spongy structure. The capillary material preferably comprises a bundle of capillaries. For example, the capillary material may comprise a plurality of fibres or threads or other fine bore tubes. The fibres or threads may be generally aligned to convey liquid aerosol-forming substrate towards the heating element. Alternatively, the capillary material may comprise sponge-like or foam-like material. The structure of the capillary material forms a plurality of small bores or tubes, through which the liquid aerosol-forming substrate can be transported by capillary action. The capillary material may extend into interstices or apertures in the heater. The heater may draw liquid aerosol-forming substrate into the interstices or apertures by capillary action.

The capillary material may comprise any suitable material or combination of materials. Examples of suitable materials are a sponge or foam material, ceramic- or graphite-based materials in the form of fibres or sintered powders, foamed metal or plastics material, a fibrous material, for example made of spun or extruded fibres, such as cellulose acetate, polyester, or bonded polyolefin, polyethylene, terylene or polypropylene fibres, nylon fibres or ceramic. The capillary material may have any suitable capillarity and porosity so as to be used with different liquid physical properties. The liquid aerosol-forming substrate has physical properties, including but not limited to viscosity, surface tension, density, thermal conductivity, boiling point and vapour pressure, which allow the liquid aerosol-forming substrate to be transported through the capillary medium by capillary action.

Alternatively, or in addition, the cartridge may contain a retention material for holding a liquid aerosol-forming substrate. The retention material may be in the first portion of the storage compartment, the second portion of the storage compartment or both the first and second portions of the storage compartment. The retention material may be a foam, a sponge or a collection of fibres. The retention material may be formed from a polymer or co-polymer. In one embodiment, the retention material is a spun polymer. The liquid aerosol-forming substrate may be released into the retention material during use. For example, the liquid aerosol-forming substrate may be provided in a capsule.

The cartridge advantageously contains liquid aerosol-forming substrate. As used herein, the term "aerosol-forming substrate" refers to a substrate capable of releasing volatile compounds that can form an aerosol. Volatile compounds may be released by heating the aerosol-forming substrate.

The aerosol-forming substrate may be liquid at room temperature. The aerosol-forming substrate may comprise both liquid and solid components. The liquid aerosol-forming substrate may comprise nicotine. The nicotine containing liquid aerosol-forming substrate may be a nicotine salt matrix. The liquid aerosol-forming substrate may comprise plant-based material. The liquid aerosol-forming substrate may comprise tobacco. The liquid aerosol-forming substrate may comprise a tobacco-containing material containing volatile tobacco flavour compounds, which are released from the aerosol-forming substrate upon heating. The liquid aerosol-forming substrate may comprise homogenised tobacco material. The liquid aerosol-forming substrate may comprise a non-tobacco-containing material. The liquid aerosol-forming substrate may comprise homogenised plant-based material.

The liquid aerosol-forming substrate may comprise one or more aerosol-formers. An aerosol-former is any suitable known compound or mixture of compounds that, in use, facilitates formation of a dense and stable aerosol and that is substantially resistant to thermal degradation at the temperature of operation of the system. Examples of suitable aerosol formers include glycerine and propylene glycol. Suitable aerosol-formers are well known in the art and include, but are not limited to: polyhydric alcohols, such as triethylene glycol, 1,3-butanediol and glycerine; esters of polyhydric alcohols, such as glycerol mono-, di- or triacetate; and aliphatic esters of mono-, di- or polycarboxylic acids, such as dimethyl dodecanedioate and dimethyl tetradecanedioate. The liquid aerosol-forming substrate may comprise water, solvents, ethanol, plant extracts and natural or artificial flavours.

The liquid aerosol-forming substrate may comprise nicotine and at least one aerosol-former. The aerosol-former may be glycerine or propylene glycol. The aerosol former may comprise both glycerine and propylene glycol. The liquid aerosol-forming substrate may have a nicotine concentration of between about 0.5% and about 10%, for example about 2%. The cartridge may comprise a housing. The housing may be formed form a mouldable plastics material, such as polypropylene (PP) or polyethylene terephthalate (PET). The housing may form a part or all of a wall of one or both portions of the liquid storage compartment. The housing and liquid storage compartment may be integrally formed. Alternatively the liquid storage compartment may be formed separately from the housing and assembled to the housing.

According to another example of the present disclosure, there is provided an aerosol-generating device. The aerosol-generating device may comprise a housing configured to receive a cartridge as described above. The housing may comprise an electrical connection for electrically connecting to the cartridge. The aerosol-generating device may further comprise a power source for supplying electrical power to the electric heater of the cartridge. The aerosol-generating device may further comprise an alternating signal source for inputting an alternating signal to the resonant circuit of the cartridge. The aerosol-generating device may further comprise control circuitry configured to control the supply of electrical power to the electric heater and to controllably vary the frequency of the alternating signal supplied to the resonant circuit. The control circuitry may be arranged to receive an output signal from the resonant circuit. The control circuitry may be further configured to determine when resonance occurs in the resonant circuit by detecting when the output signal reaches a predetermined threshold value. The control circuitry may be further configured to determine the frequency at which resonance occurs. The control circuitry may be further configured to identify the cartridge based on the determined resonant frequency.

Advantageously, the aerosol-generating device can be used with one of the above-described cartridges and is able to identify the cartridge so that appropriate aerosolisation conditions can be used for the particular aerosol-forming substrate contained within the cartridge. Furthermore, the aerosol-generating device is advantageously able to detect unauthorised or counterfeit cartridges which do not present expected resonant frequencies to the device.

The predetermined threshold value used for determining when resonance occurs may comprise a maximum or a minimum of the output signal.

The control circuitry may be configured to sweep the frequency of the alternating signal over a predetermined frequency range within a predetermined time period. It has advantageously been found that sweeping a predetermined frequency range is an effective way of detecting expected resonant frequencies within the frequency range. The control circuitry of the aerosol-generating device can configured to do this quickly and efficiently.

The frequency of the alternating signal may be swept over a predetermined frequency range within a predetermined time period of 5 milliseconds or less. This allows for rapid detection of the resonant frequency and cartridge identification. Furthermore, a 5 millisecond detection time is sufficiently short that cartridge identification could be carried out during the power-off part of a pulse width modulated power supply being supplied to the heater, for example, a pulse width modulated power supply having a 10 millisecond period and a 50 percent duty cycle.

As an alternative to continuously sweeping a predetermined frequency range, the control circuitry of the aerosol-generating device may be configured to monitor a plurality of predetermined frequencies or frequency bands of a frequency range to determine whether resonance is occurring at those frequencies or within the frequency bands. The control circuitry may be configured to sequentially move or hop between frequencies or frequency bands to determine the resonant frequency and hence the identity of the cartridge. Advantageously, this may reduce the time taken to determine the resonant frequency and may reduce energy consumption during identification of the cartridge.

The peak voltage of the alternating signal supplied to the resonant circuit may be 2 Volts (V) or less, preferably 1.5 V or less and more preferably 1 V or less. Advantageously, by using a peak voltage of 2 V or less for the alternating signal, any significant heating of the heater can be avoided and therefore energy losses can be reduced or kept to a minimum.

The control circuitry may comprise a microprocessor. The microprocessor may be a programmable microprocessor, a microcontroller, or an application specific integrated chip (ASIC) or other electronic circuitry capable of providing control. The control circuitry may comprise further electronic components. For example, in some embodiments, the control circuitry may comprise any of: sensors, switches, display elements. Power may be supplied to the aerosol-generating element continuously following activation of the device or may be supplied intermittently, such as on a puff-by-puff basis. The power may be supplied to the aerosol-generating element in the form of pulses of electrical current, for example, by means of pulse width modulation (PWM). The power source may be a battery. The battery may be a lithium iron phosphate battery, within the device. As an alternative, the power source may be another form of charge storage device such as a capacitor.

The control circuitry may comprise a resonance detection circuit for detecting when resonance is occurring. The resonance detection circuit may comprise a peak detection circuit for detecting when a value of the output signal reaches a peak value or a predetermined threshold value. As used herein, the term "peak detection circuit" is used to refer to a circuit that can detect both a maximum value or maximum threshold value as well as a minimum value or minimum threshold value.

In some examples, the control circuitry is configured to interrogate a look-up table stored in a memory of the control circuitry, and compare the determined resonant frequency with one or more reference resonant frequencies stored in the look-up table.

Put in another way, the control circuitry may comprise a memory storing one or more reference resonant frequency values, each reference resonant frequency value being associated with a particular cartridge identity. The control circuitry is configured to compare a determined resonant frequency value measured from the resonant circuit to the reference resonant frequency values stored in the look-up table. Where the determined resonant frequency value matches a reference resonant frequency value stored in the look-up table, the cartridge identity is determined to be the cartridge identity associated with the matched reference resonant frequency value.

It will be appreciated that ranges of reference frequency values may be stored in the look-up table, and each range of reference resonant frequency values may be associated with a particular cartridge identity. When a determined resonant frequency value is compared to the ranges of resonant frequency values, and the determined resonant frequency value falls within a range of reference resonant frequency values, the cartridge identity is determined to be the cartridge identity associated with the range of reference frequency values in which the determined resonant frequency value fell.

The control circuitry may be configured to control the supply of power from the power source of the aerosol-generating device to the electric heater of the cartridge based on the determined identity of the cartridge.

In some examples, the control circuitry may be configured to prevent power from being supplied from the power supply to the electric heater if the identity of the cartridge is not recognised. In other words, if the determined resonant frequency does not equal an expected resonant frequency value, the control circuitry may be configured to prevent power from being supplied from the power source to the electric heater. In embodiments in which a look-up table of reference resonant frequency values is stored in a memory of the controller, the control circuitry may be configured to prevent power from being supplied to the electric heater when the determined resonant frequency does not match any of the stored reference resonant frequency values. Advantageously, preventing power from being supplied to the electric heaters when the determined resonant frequency does not match an expected resonant frequency may prevent or inhibit unauthorised cartridges from being used with an aerosol-generating device.

In some examples, the control circuitry may be configured to adjust the power supplied from the power supply to the electric heater based on the determined identity of the cartridge. This may enable the aerosol-generating device to heat different aerosol-forming substrates, contained in different cartridges, to different temperatures.

Advantageously, configuring the control circuitry to adjust the power supplied to the electric heater based on the determined cartridge identity may enable the aerosol-generating device to be used with different types of cartridge, containing different aerosol-forming substrates. Since different aerosol-forming substrates may require heating to different temperatures to achieve an aerosol with the desired characteristics, adjusting the power supplied to the heater based on the determined cartridge identity may ensure that the aerosol-generating device is configured to generate an optimal aerosol from different cartridges, containing different aerosol-forming substrates.

In some examples, the control circuitry may be configured to supply a first power to the electric heater when a first cartridge identity is determined, and the control circuitry may be further configured to supply a second power, different to the first power, to the electric heater when a second cartridge identity, different to the first cartridge identity, is determined.

The power source may be a DC power supply. The power source may be a battery. The battery may be a Lithium based battery, for example a Lithium-Cobalt, a Lithium-Iron-Phosphate, a Lithium Titanate or a Lithium-Polymer battery. The battery may be a Nickel-metal hydride battery or a Nickel cadmium battery. The power source may be another form of charge storage device such as a capacitor. The power source may be rechargeable and be configured for many cycles of charge and discharge. The power source may have a capacity that allows for the storage of enough energy for one or more user experiences; for example, the power source may have sufficient capacity to allow for the continuous generation of aerosol for a period of about six minutes, corresponding to the typical time taken to smoke a conventional cigarette, or for a period that is a multiple of six minutes. In another example, the power source may have sufficient capacity to allow for a predetermined number of puffs or discrete activations of the atomiser assembly.

The aerosol-generating device may comprise a housing. The housing may be elongate. The housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. The material is preferably light and non-brittle.

According to another example of the present disclosure, there is provided an aerosol-generating system. The aerosol-generating system may comprise the above-described aerosol-generating device and the above-described cartridge.

The aerosol-generating system may be a handheld aerosol-generating system configured to allow a user to puff on a mouthpiece to draw an aerosol through a mouth end opening. The aerosol-generating system may have a size comparable to a conventional cigar or cigarette. The aerosol-generating system may have a total length between about 30 mm and about 150 mm. The aerosol-generating system may have an external diameter between about 5 mm and about 30 mm.

The invention is defined in the claims. However, below there is provided a non-exhaustive list of non-limiting examples. Any one or more of the features of these examples may be combined with any one or more features of another example, embodiment, or aspect described herein.

Example Ex1: A cartridge for an aerosol-generating device, the cartridge comprising: an aerosol-forming substrate; and a resonant circuit; wherein the resonant circuit is configured to resonate at a predetermined resonant frequency, wherein the predetermined resonant frequency is associated with an identity of the cartridge.

Example Ex2: A cartridge according to example Ex1, further comprising an electric heater for heating the aerosol-forming substrate.

Example Ex3: A cartridge according to example Ex2, wherein the resonant circuit is connected in parallel with the electric heater.

Example Ex4: A cartridge according to any of examples Ex1 to Ex3, wherein the resonant circuit comprises a capacitor and an inductor.

Example Ex5: A cartridge according to example Ex4, wherein the capacitor and inductor are connected in series.

Example Ex6: A cartridge according to example Ex4 or Ex5, wherein the predetermined resonant frequency of the resonant circuit is determined by the capacitance of the capacitor, and wherein the predetermined resonant frequency can be changed by changing the capacitance of the capacitor.

Example Ex7: A cartridge according to any preceding example, wherein the predetermined resonant frequency is in the range 10 kHz to 100 MHz, preferably in the range 100 kHz to 20 MHz and more preferably in the range 1 MHz to 11 MHz.

Example Ex8: A cartridge according to any of examples Ex4 to Ex7, wherein the capacitance of the capacitor is in the range 0.1 nF to 10 nF.

Example Ex9: A cartridge according to any of examples Ex4 to Ex8, wherein the resonant circuit comprises a plurality of capacitors arranged in parallel, and wherein the combined capacitance of the plurality of capacitors is used to produce resonance.

Example Ex10: A cartridge according to any of examples Ex4 to Ex9, wherein the resonant circuit is arranged on a printed circuit-board (PCB), and wherein the inductor is formed directly on the PCB as a conductive track.

Example Ex11: A cartridge according to any of examples Ex1 to Ex3, wherein the resonant circuit comprises a capacitor connected in parallel with the heater, and the resonant circuit is configured to use a parasitic inductance of the resonant circuit in combination with the capacitance of the capacitor to produce resonance.

Example Ex12: A cartridge according to example Ex11, wherein the predetermined resonant frequency is in the range 100 kHz to 100 MHz and preferably in the range 1 MHz to 50 MHz.

Example Ex13: A cartridge according to example Ex11 or Ex12, wherein the capacitance of the capacitor is in the range 1 nF to 300 nF.

Example Ex14: A cartridge according to any of examples Ex1 to Ex5, wherein the predetermined resonant frequency of the resonant circuit is determined by the inductance of the inductor, and wherein the resonant frequency can be changed by changing the inductance of the inductor.

Example Ex15: A cartridge according to example Ex14, wherein the inductance of the inductor is in the range 0.1 nH to 330 nH.

Example Ex16: A cartridge according to any preceding example, wherein the resonant circuit is arranged to be connected to an alternating signal source and is configured to resonate when the predetermined resonant frequency substantially equals the frequency of the alternating signal.

Example Ex17: A cartridge according to any preceding example, wherein the electric heater is a fluid permeable heater, and preferably a mesh heater.

Example Ex18: An aerosol-generating device comprising: a housing configured to receive a cartridge according to any of examples Ex1 to Ex17, wherein the housing comprises an electrical connection for electrically connecting to the cartridge; a power source for supplying electrical power to the electric heater of the cartridge; an alternating signal source for inputting an alternating signal to the resonant circuit of the cartridge; and control circuitry configured to control the supply of electrical power to the electric heater and to controllably vary the frequency of the alternating signal supplied to the resonant circuit; wherein the control circuitry is arranged to receive an output signal from the resonant circuit; and wherein the control circuitry is further configured to: determine when resonance occurs in the resonant circuit by detecting when the output signal reaches a predetermined threshold value; determine the frequency at which resonance occurs; and identify the cartridge based on the determined resonant frequency.

Example Ex19: An aerosol-generating device according to example Ex18, wherein the control circuitry is configured to sweep the frequency of the alternating signal over a predetermined frequency range within a predetermined time period, wherein the predetermined time period is 5 milliseconds or less.

Example Ex20: An aerosol-generating device according to example Ex18 or Ex19, wherein the peak voltage of the alternating signal supplied to the resonant circuit is 2 V or less, preferably 1.5 V or less and more preferably 1 V or less.

Example Ex21: An aerosol-generating device according to any of examples Ex18 to Ex20, wherein the predetermined threshold value comprises a maximum or a minimum of the output signal.

Example Ex22: An aerosol-generating device according to any of examples Ex18 to Ex21, wherein the control circuitry of the aerosol-generating device may be configured to monitor a plurality of predetermined frequencies or frequency bands of a frequency range to determine whether resonance is occurring at those frequencies or within the frequency bands.

Examples will now be further described with reference to the figures in which.

Figure 1:
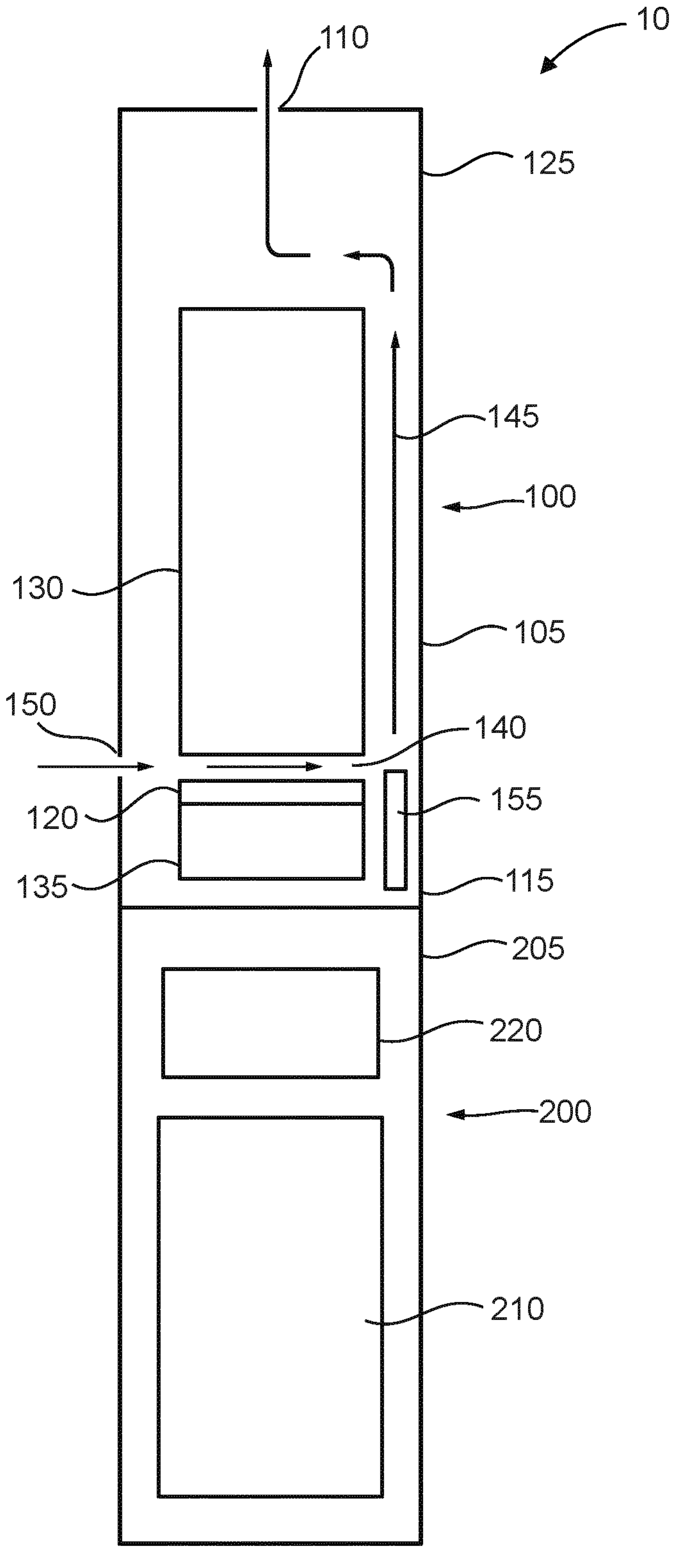
FIG. 1 is a schematic illustration of an example aerosol-generating system comprising a cartridge and an aerosol-generating device.

FIG. 1 is a schematic illustration of an example aerosol-generating system 10. The aerosol-generating system 10 comprises two main components, a cartridge 100 and a main body part or aerosol-generating device 200. A connection end 115 of the cartridge 100 is removably connected to a corresponding connection end 205 of the aerosol-generating device 200. The connection end 115 of the cartridge 100 and connection end 205 of the aerosol-generating device 200 each have electrical contacts or connections (not shown) which are arranged to cooperate to provide an electrical connection between the cartridge 100 and the aerosol-generating device 200. The aerosol-generating device 200 contains a power source in the form of a battery 210, which in this example is a rechargeable lithium ion battery, and control circuitry 220. The aerosol-generating system is portable and has a size comparable to a conventional cigar or cigarette. A mouthpiece 125 is arranged at the end of the cartridge 100 opposite the connection end 115.

The cartridge 100 comprises a housing 105 containing an electric heater 120 and a liquid storage compartment having a first portion 130 and a second portion 135. A liquid aerosol-forming substrate is held in the liquid storage compartment. Although not illustrated in FIG. 1, the first portion 130 of the liquid storage compartment is connected to the second portion 135 of the liquid storage compartment so that liquid in the first portion 130 can pass to the second portion 135. The electric heater 120 receives liquid from the second portion 135 of the liquid storage compartment. In this embodiment, the electric heater 120 comprises a fluid permeable heating element, for example, a mesh heater. The cartridge 100 further comprises a resonant circuit 155 mounted on a printed circuit board (PCB) which is arranged to the side of the second portion 135 of the liquid storage compartment and is connected via conductors (not shown) in parallel with the heater 120.

An air flow passage 140, 145 extends through the cartridge 100 from an air inlet 150 formed in a side of the housing 105 past the heater 120 and from the heater 120 to a mouthpiece opening 110 formed in the housing 105 at an end of the cartridge 100 opposite to the connection end 115.

The components of the cartridge 100 are arranged so that the first portion 130 of the liquid storage compartment is between the heater 120 and the mouthpiece opening 110, and the second portion 135 of the liquid storage compartment is positioned on an opposite side of the heater 120 to the mouthpiece opening 110. In other words, the heater 120 lies between the two portions 130, 135 of the liquid storage compartment and receives liquid from the second portion 135. The first portion 130 of the liquid storage compartment is closer to the mouthpiece opening 110 than the second portion 135 of the liquid storage compartment. The air flow passage 140, 145 extends past the heater 120 and between the first 130 and second 135 portions of the liquid storage compartment.

The aerosol-generating system 10 is configured so that a user can puff or draw on the mouthpiece 125 of the cartridge to draw aerosol into their mouth through the mouthpiece opening 110. In operation, when a user puffs on the mouthpiece 125, air is drawn through the airflow passage 140, 145 from the air inlet 150, past the heater 120, to the mouthpiece opening 110. The control circuitry 220 controls the supply of electrical power from the battery 210 to the cartridge 100 when the system is activated. This in turn controls the amount and properties of the vapour produced by the heater 120. The control circuitry 220 may include an airflow sensor (not shown) and the control circuitry 220 may supply electrical power to the heater 120 when user puffs on the cartridge 100 are detected by the airflow sensor. This type of control arrangement is well established in aerosol-generating systems such as inhalers and e-cigarettes. So when a user puffs on the mouthpiece opening 110 of the cartridge 100, the heater 120 is activated and generates a vapour that is entrained in the air flow passing through the air flow passage 140. The vapour cools within the airflow in passage 145 to form an aerosol, which is then drawn into the user's mouth through the mouthpiece opening 110.

In operation, the mouthpiece opening 110 is typically the highest point of the system. The construction of the cartridge 100, and in particular the arrangement of the heater 120 between first and second portions 130, 135 of the liquid storage compartment, is advantageous because it exploits gravity to ensure that the liquid substrate is delivered to the heater 120 even as the liquid storage compartment is becoming empty, but prevents an oversupply of liquid to the heater 120 which might lead to leakage of liquid into the air flow passage 140.

Figure 2:
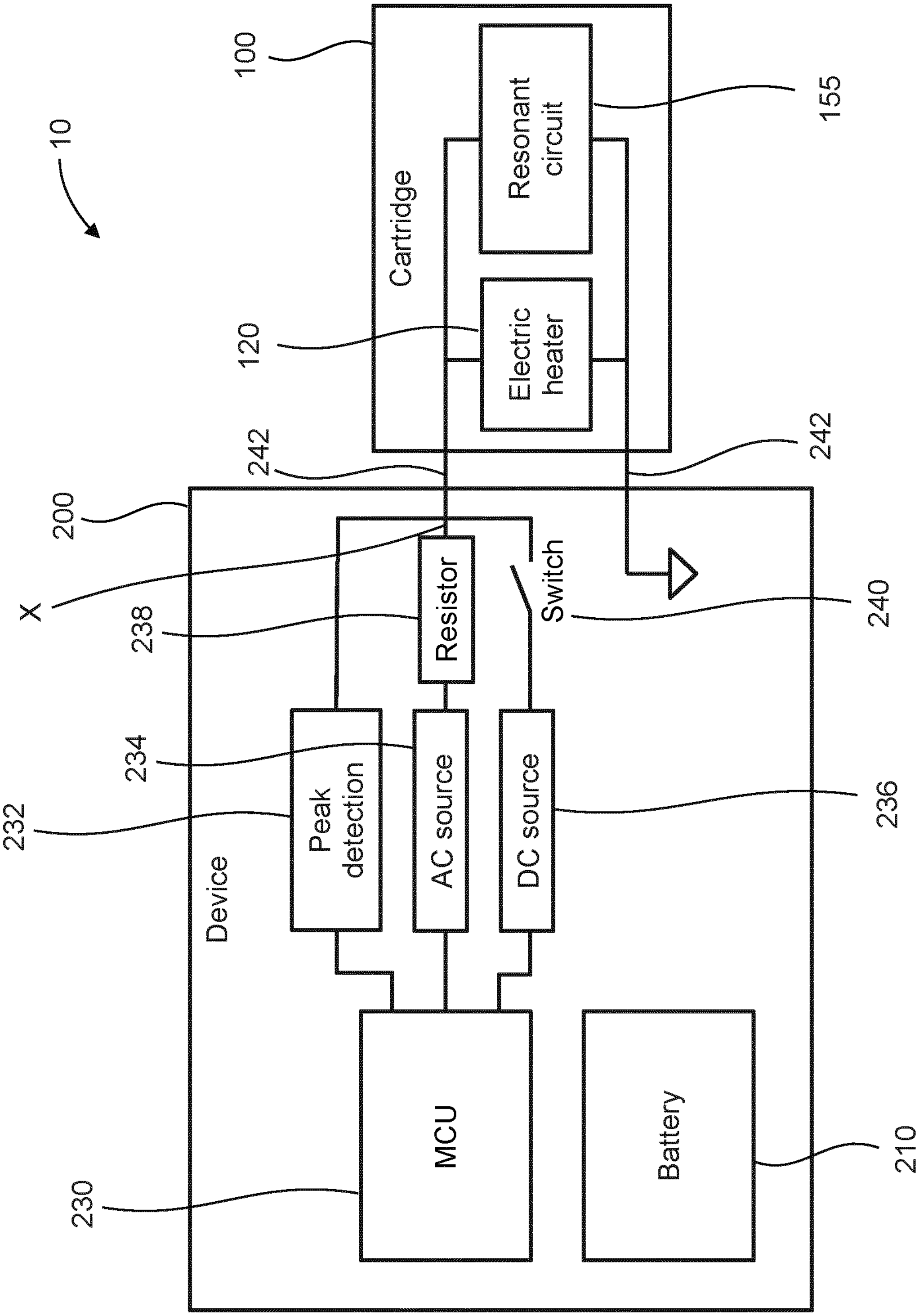
FIG. 2 is a block diagram showing the main electric and electronic components of an example aerosol-generating system.

FIG. 2 is a block diagram showing the main electric and electronic components of an example aerosol-generating system 10 comprising a cartridge 100 and an aerosol-generating device 200. The cartridge 100 comprises an electric heater 120 and a resonant circuit 155. The resonant circuit 155 is configured to resonate at a predetermined resonant frequency, which resonant frequency is associated with an identity of the cartridge 100 or the aerosol-forming substrate (not shown) contained within the cartridge 100. By determining the resonant frequency of the resonant circuit 155, the aerosol-generating device 200 is able to identify the cartridge 100 and its contents and apply appropriate aerosolisation conditions. For example, the aerosol-generating device 200 may apply a suitable heating profile for the particular liquid aerosol-forming substrate contained in the cartridge 100.

The resonant circuit 155 is connected in parallel across the electric heater 120. By connecting the resonant circuit 155 in parallel with the heater 120, only two electrical connections 242 are required to connect the cartridge 100 to the aerosol-generating device 200. The two electrical connections 242 can be used to supply power to the heater 120, to provide an input alternating signal to the resonant circuit 155 and to receive an output signal from the resonant circuit 155. Different example resonant circuits of the present disclosure are described in more detail below.

The aerosol-generating device 200 comprises a battery 210, which acts as a power source, and a microcontroller (MCU) 230, which forms part of the control circuitry of the aerosol-generating device 200. The microcontroller 230 is configured to control the supply of electrical power to the electric heater 120. The microcontroller 230 controls the supply of a DC voltage source 236 to the heater 120. The microcontroller 230 modulates the DC voltage source 236 through pulse width modulation (PWM) to provide power to the electric heater120 as a series of pulses. The DC voltage source 236 can be selectively connected to the electric heater 120 by a switch 240, which may be a transistor or other suitable electronic switch. No passive components which can generate heat, such as resistors or inductors, are connected in series between the DC voltage source and the electric heater 120. This helps to reduce energy losses.

The microcontroller 230 also controls the provision of an alternating signal source or AC source 234 to the cartridge 100, in particular as an input signal to the resonant circuit 155. The microcontroller 230 is able to vary or sweep the frequency of the alternating signal supplied to the resonant circuit 155 over a frequency range containing the resonant frequency of the resonant circuit 155. A resistor 238 is arranged within the aerosol-generating device so that it is connected in series between the alternating signal source 234 and the resonant circuit 155 in the cartridge 100. The resistor 238 forms part of a potential divider with the components of the resonant circuit 155 and allows a measurement voltage to be taken off the circuit at a point X between the resistor 238 and resonant circuit 155.

Although FIG. 2 shows the alternating signal source or AC source 234 and the DC voltage source 236 as separate blocks in the diagram, this has been done solely for clarity and in practice both of these sources are provided by the microcontroller 230, potentially with a few ancillary components such as transistors for sourcing larger currents. However, it will be appreciated that in other examples, separate AC and DC sources may be provided.

The aerosol-generating device 200 further comprises a peak detection circuit 232 which forms a further part of the control circuitry of the aerosol-generating device 200. The peak detection circuit 232 receives an output signal from the resonant circuit 155 and provides its own output to the microcontroller 230. To receive the output signal from the resonant circuit 155, the peak detection circuit 232 measures the voltage at point X between the resistor 238 and resonant circuit 155. The peak detection circuit 232 is able to determine or measure the peak amplitude that occurs in the output signal from the resonant circuit 155 or when the output signal reaches a predetermined threshold value. As mentioned above, when the resonant circuit is resonating at its resonant frequency, the output signal oscillates with a greater amplitude than at other frequencies. Therefore, the microcontroller 230 varies or sweeps the frequency of the alternating signal supplied to the resonant circuit 155 over a predetermined frequency range within which the resonant frequency is expected to be and monitors at what frequency the output signal has its greatest amplitude to determine the resonant frequency of the resonant circuit 155 and identify the cartridge 100.

Depending on the configuration of the resonant circuit 155 and the point at which its output signal is measured, it is possible that the output signal may have a minimum amplitude at resonance. Therefore, the peak detection circuit 232 is also able to measure the minimum amplitude that occurs in the output signal in order to determine the resonant frequency.

Figure 3A:
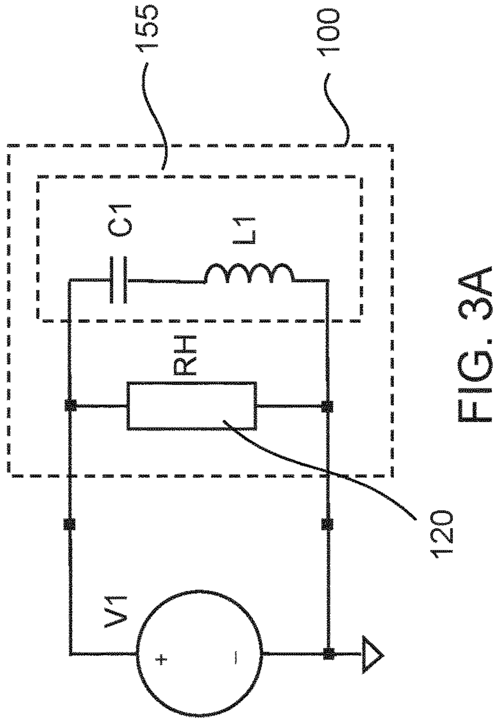
FIG. 3A shows a schematic circuit diagram of an example cartridge comprising a resonant circuit, in which the example cartridge is connected to a DC voltage source.

FIG. 3A shows a schematic diagram of an example cartridge 100 comprising a resonant circuit 155. The resonant circuit 155 comprises a capacitor C1 connected in series with an inductor L1. The resonant circuit 155 is arranged in parallel with the heater 120. The heater is a resistive heater and is therefore represented in FIG. 3A as a resistor RH. The resistance of the heater 120 is 0.69 Ohms. The cartridge 100 is connected to a DC voltage source V1 which provides a pulse width modulated DC voltage across the parallel arrangement of the heater 120 and resonant circuit 155. The pulse width modulation is controlled by a microcontroller (not shown). In the described example, the pulse width modulated DC voltage has an amplitude of 3.6 Volts, a period of 10 milliseconds and a duty cycle of 50 percent. This results in a pulsed current in the heater 120 of approximately 5.2 Amps.

When the cartridge 100 is connected to the DC voltage source V1, current flows only in the resistive heater 120. No current flows in the resonant circuit 155 because it is arranged in parallel with the heater 120 and the capacitor C1 in the resonant circuit blocks DC voltage, that is, it effectively acts as an open circuit for DC voltage. Thus, power is only dissipated in the heater 120 and not in the resonant circuit 155, which makes the arrangement energy efficient.

The DC voltage source V1 can be controlled to control the heating profile which is applied to a particular cartridge. Once the cartridge 100 has been identified in accordance with the procedures described below, a suitable heating profile for the particular liquid aerosol-forming substrate contained in the cartridge 100 can be applied. For different cartridges, the heating profile can be varied by varying the characteristics of the pulse width modulated DC voltage applied to the cartridge. For example, the duty cycle of the pulse width modulated DC voltage or the amount of time the pulse width modulated DC voltage is applied can be varied.

Figure 3B:
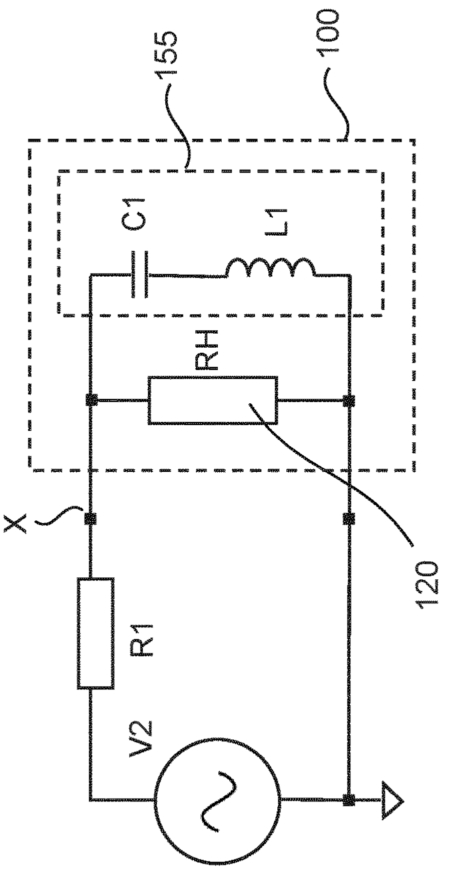
FIG. 3B shows a schematic circuit diagram of the cartridge of FIG. 3A, in which the cartridge is connected to an alternating signal source.

FIG. 3B shows a schematic circuit diagram of the cartridge 100 of FIG. 3A in which the cartridge is connected to an alternating voltage source or alternating signal source V2 that inputs an alternating signal to the resonant circuit 155. The alternating signal source V2 is controlled by a microcontroller (not shown) and has an amplitude of 1 Volt peak. The microcontroller is able to vary or sweep the frequency of the alternating signal of the alternating signal source V2 in order to detect resonance and therefore determine the identity of the cartridge. The frequency can be swept in the range 1 megahertz to 13 megahertz and due to the relatively high frequencies being used, it was found that the frequency sweep could be carried out in a relatively short period of time, that is, 240 microseconds. When the frequency of the input alternating signal equals the natural resonant frequency of the resonant circuit 155, the resonant circuit 155 resonates.

The resonant circuit 155 is configured to resonate at a predetermined resonant frequency to allow the cartridge 100 to be identified. As set out in Equation (1) above, the resonant frequency is a function of the capacitance of the capacitor C1 and the inductance of the inductor L1. In this described example, the predetermined resonant frequency of the resonant circuit 155 is determined by the capacitance of the capacitor C1. Different capacitors having different capacitance values can be used to produce different resonant frequencies for different cartridges. The inductance of the inductor L1 is fixed at 1 microhenry. To produce different resonant frequencies, ten different capacitor values taken from the E12 series of capacitor values were used for capacitor C1. The C1 capacitance values and the resulting resonant frequencies are shown in Table 1.

TABLE 1

| | Capacitance (nanofarads) | | | | | | | | | |
|---|---|---|---|---|---|---|---|---|---|---|
| | 8.2 | 5.6 | 3.9 | 2.7 | 1.8 | 1.2 | 0.82 | 0.56 | 0.39 | 0.27 |
| Resonant freq. (megahertz) | 1.76 | 2.13 | 2.56 | 3.07 | 3.76 | 4.61 | 5.57 | 6.74 | 8.08 | 9.71 |

As can be seen from Table 1, the inventors were able to achieve ten different resonant frequencies with sufficient spacing between the frequencies to clearly distinguish ten different cartridges. However, it will be appreciated that more resonant frequencies can be achieved by using more capacitor values.

Figure 4:
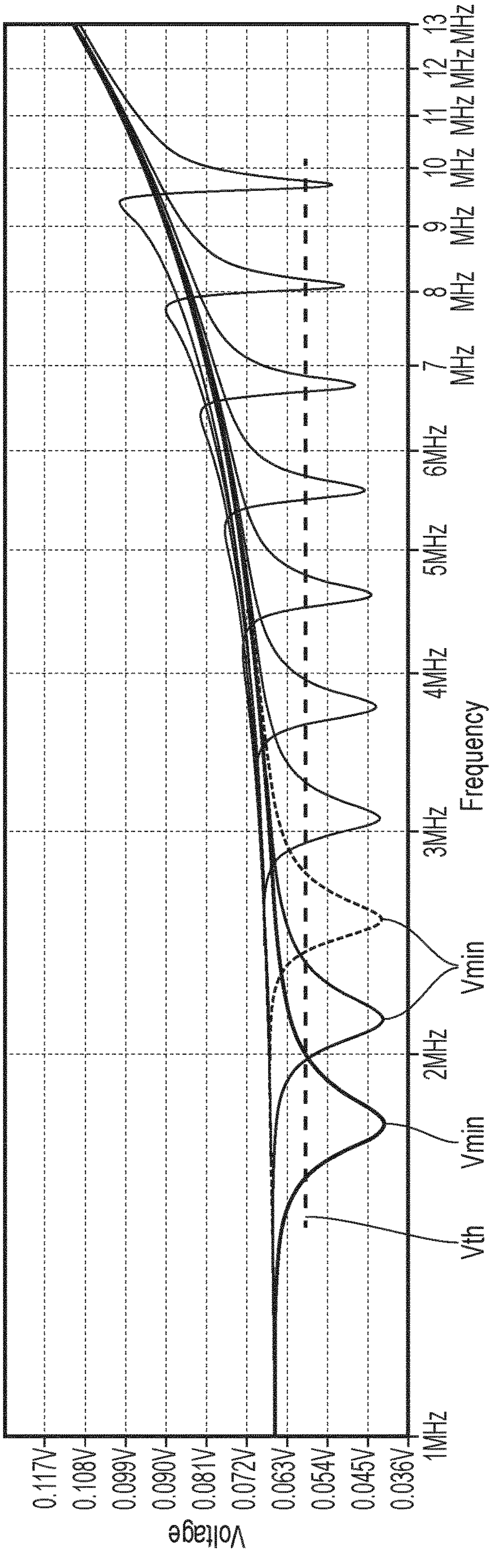
FIG. 4 is a graph of frequency versus voltage showing the frequency response of the resonant circuit of FIG. 3B when using different capacitor values.

FIG. 4 is a graph of frequency versus voltage showing the frequency response of the resonant circuit 155 of FIG. 3B. In FIG. 4, there is a frequency response curve for each of the different capacitor values of Table 1. The output signal for resonant circuit 155 was measured at point X in the circuit of FIG. 3B, that is, between resistor R1 and the resonant circuit 155. Resistor R1 forms part of a potential divider together with resonant circuit 155 so that a voltage can be measured at point X. Resonance occurs when the reactance of C1 and the reactance of L1 are equal in magnitude but opposite in phase such that the two reactances cancel each other. Therefore, at resonance, the impedance of the resonant circuit is at a minimum and hence the voltage measured at point X is a minimum at resonance. For each of the frequency response curves in FIG. 4, a voltage minimum Vmin can be seen occurring at each of the resonant frequencies in Table 1, which correspond to the different capacitor values used. The voltage minimums occur over a relatively small section of the entire length of the frequency response curves and are therefore easily discernible and detectable.

The minimum voltages can be detected by a peak detection circuit. The frequency at which the minimum voltage is detected provides an indication of the resonant frequency of the resonant circuit and the identity of the cartridge. Alternatively, the resonant frequency can be determined by configuring an aerosol-generating device to detect when the output signal drops below a threshold voltage Vth denoted by a horizontal dotted line in FIG. 4.

Referring again to FIG. 3B, when alternating signal source V2 is connected to the cartridge 100 to detect resonance and determine the identify the cartridge, the alternating signal splits between the heater 120 and the resonant circuit 155. In contrast to a DC voltage, an alternating signal is able to pass through the capacitor C1 of the resonant circuit. During cartridge identification, the peak current flowing through the heater 120 was measured as being approximately 100 milliamps. As mentioned above, the alternating signal source V2 has an amplitude of 1 Volt peak. Therefore, the power consumed by the heater 120 during cartridge identification can be determined from Equation (2) below.

$$P=I_{RMS}\times V_{RMS} \tag{2}$$

where P is power, $I_{RMS}$ ms is the root mean square current which is equal to 0.707×peak current and $V_{RMS}$ is root mean square voltage which is equal to 0.707×peak voltage.

Furthermore, the energy consumed by the heater 120 during cartridge identification can be determined from Equation (3) below.

$$E=P\times t \tag{3}$$

where E is energy, P is power and t is time or duration of operation.

Therefore, based on a peak current of 100 milliamps and a peak voltage of 1 Volt, the power consumed by the heater 120 during cartridge identification can be calculated as being 50 milliwatts. Furthermore, based on an operation time for cartridge identification of 240 microseconds, the energy consumed by the heater 120 during cartridge identification can be calculated as being 12 microjoules. Such a small amount of energy will not heat the heater to any appreciable extent and therefore the energy efficiency of cartridge identification is improved by avoiding energy losses in the heater 120.

Due to the short period of time required to perform cartridge identification, it could be performed during the voltage-off time of a pulse width modulated DC voltage used to power the heater. The pulse width modulated DC voltage of DC voltage source V1 (see FIG. 3A) has a period of 10 milliseconds and a duty cycle of 50 percent. The voltage-off time is therefore 5 milliseconds, which is ample time to perform cartridge identification because cartridge identification only takes 240 microseconds.

Figure 5:
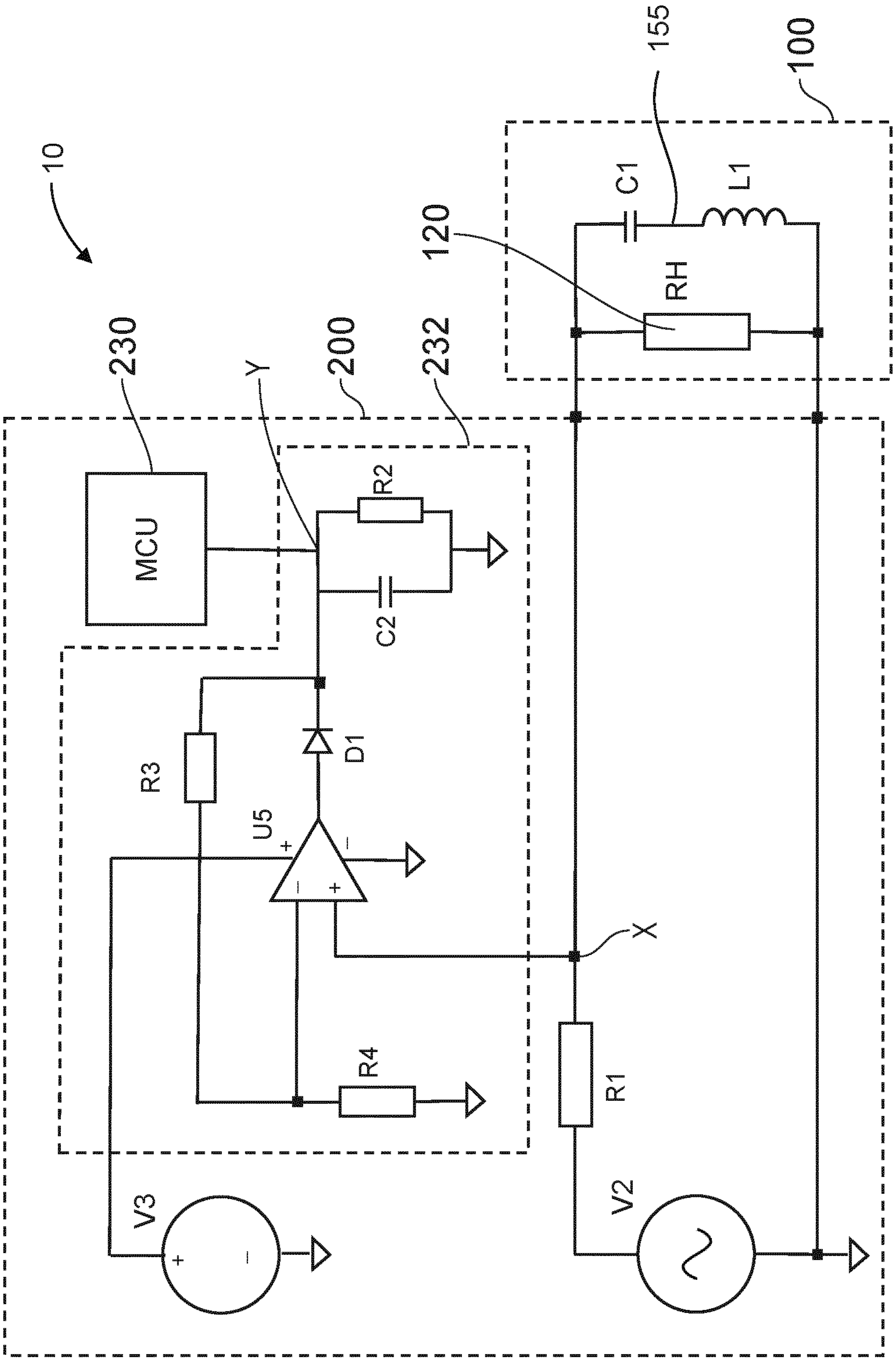
FIG. 5 is a schematic diagram of an example circuit for an aerosol-generating system for determining the resonant frequency of a resonant circuit of a cartridge. The cartridge is the example cartridge of FIGS. 3A and 3B.

FIG. 5 is a schematic diagram of an example circuit for an aerosol-generating system 10 for determining the resonant frequency of a resonant circuit 155 of a cartridge 100. The cartridge 100 is the example cartridge of FIGS. 3A and 3B. The lower part of the circuit of FIG. 5 shows a cartridge comprising a resonant circuit 155 and a heater 120 connected to an alternating signal source V2 in order to identify the cartridge 100. The arrangement and operation of this part of the circuit of FIG. 5 is the same as the circuit shown in FIG. 3B and for conciseness is not repeated here.

The circuit of FIG. 5 further comprises a peak detection circuit 232 for detecting the maximum or minimum amplitude of the output signal from the resonant circuit 155. The peak detection circuit 232 is arranged within the aerosol-generating device 200 of aerosol-generating system 10. The peak detection circuit 232 comprises an operational amplifier U5 for amplifying a signal input to the peak detection circuit 232, a forward biased diode D1 for half-way rectifying an input alternating signal and a capacitor C2 for holding or storing a voltage of the signal received from the diode. The non-inverting input (+) of the operational amplifier acts as an input to the peak detection circuit 232 and an output from the peak detection circuit 232 is taken from an upstream terminal of the capacitor C2, that is, the terminal of the capacitor C2 connected to the diode D1. The peak detection circuit 232 further comprises a resistor R2 having a value of 10 ohms for discharging of the capacitor to ground.

Any suitable operational amplifier may be used. For example, the described example uses an LTC6244 operational amplifier manufactured by Analog Devices of Massachusetts, USA. The operational amplifier U5 is powered by a DC voltage source V3, which provides 3.1 volts. Two resistors, R3 and R4 which have values of 150 kilo-ohms and 10 kilo-ohms respectively, are provided as part of a negative feedback loop for the operational amplifier. The gain of the amplifier can be determined in accordance with Equation (4) below:

$$\text{Gain}=1+R3/R4 \tag{4}$$

In use, the output signal from the resonant circuit 155 is taken at point X in the circuit, i.e. the mid-point of the voltage divider formed by resistor R1 and the resonant circuit 155 and fed as an input to the non-inverting input of the operational amplifier U5 of the peak detection circuit 232. The signal is half-wave rectified by diode D1 to form a series of positive pulses and the voltage of successive pulses is held or stored by capacitor C2. The output of the peak detection circuit 232, that is, the voltage stored by capacitor C2, is fed to an analogue to digital converter input of the microcontroller 230 of the aerosol-generating device 200, which periodically measures or samples the voltage stored by capacitor C2. Once the voltage has been sampled the capacitor C2 is discharged to electrical ground in preparation for taking the next sample.

The microcontroller 230 samples the output from the peak detection circuit over the time period taken to sweep the frequency of the alternating signal over the desired frequency range, which in this case is 1 megahertz to about 10.6 megahertz and takes about 240 microseconds. In this manner, the microcontroller 230 obtains a profile of the amplitude of the output signal from the resonant circuit over the range of swept frequencies. The samples are analysed by the microcontroller 230 to determine a minimum value. Since the microcontroller 230 also controls alternating signal source V2 and the frequency of the alternating signal being provided to the resonant circuit 155 of the cartridge 100, the microcontroller 230 is able to determine the frequency at which the minimum value of the output from the peak detection circuit 232 was detected. This frequency is the frequency at which resonance occurred in the resonant circuit 155 and indicates the identity of the cartridge.

Figure 6A:
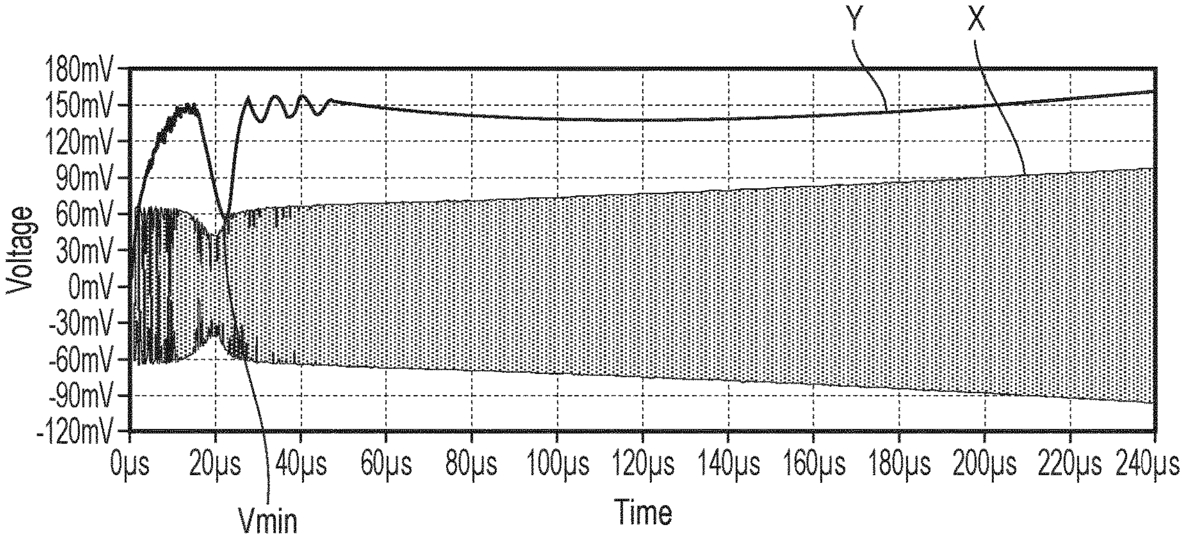
FIGS. 6A to 6C are graphs of voltage versus time showing the detection of resonance for differing values of capacitor in a resonant circuit.
Figure 6B:
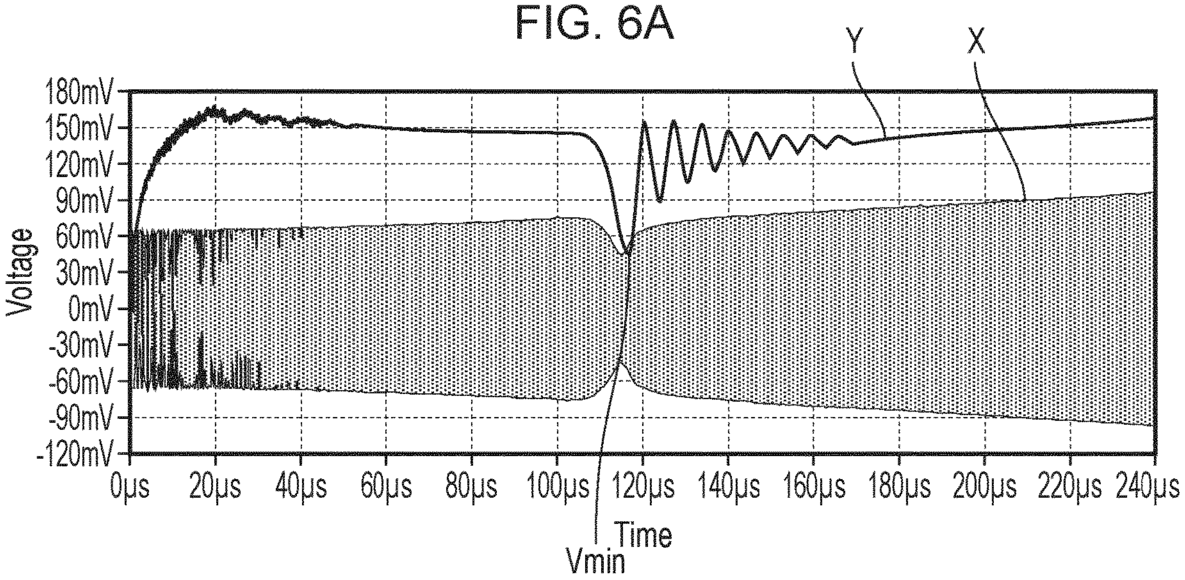
Figure 6C:
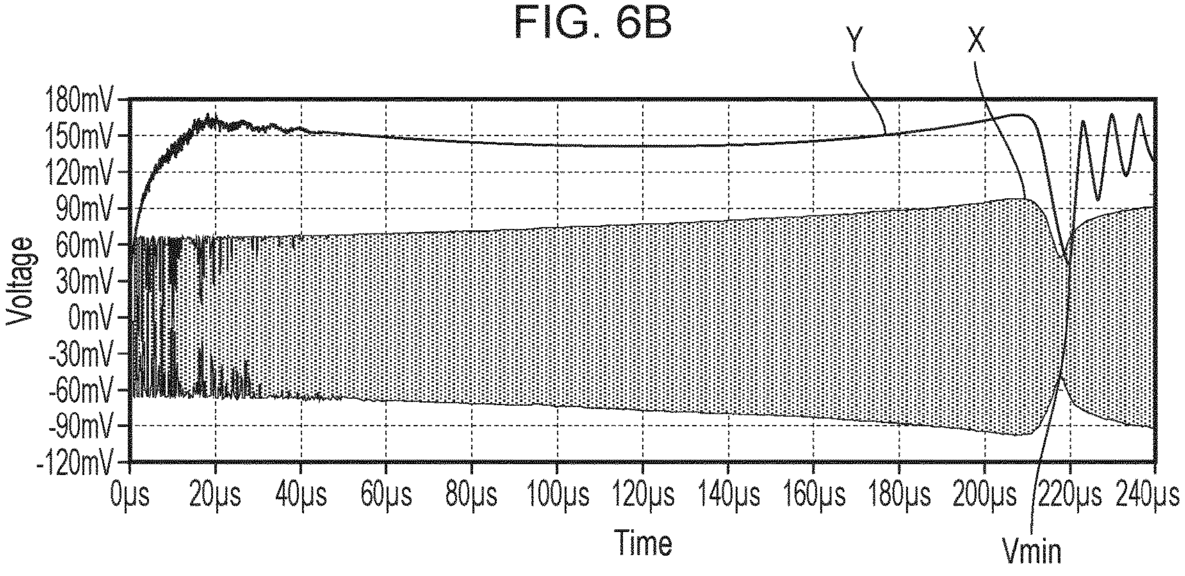

FIGS. 6A to 6C are graphs of voltage versus time showing the detection of resonance for different values of capacitor in the resonant circuit 155 in the cartridge 100 of FIG. 5. The graphs show two curves: curve X which corresponds to the output signal from the resonant circuit 155 measured at point X in the circuit of FIG. 5; and curve Y which corresponds to the output from the peak detection circuit 232 at point Y in the circuit of FIG. 5.

FIG. 6A shows the output signals from the resonant circuit 155 (curve X) and peak detection circuit 232 (curve Y) when a capacitor value of 8.2 nanofarads is used in the resonant circuit 155. As shown in Table 1 above, this capacitance value produces a resonant frequency of 1.76 megahertz. The graph of FIG. 6A shows a voltage minimum Vmin occurring relatively early in curve Y, that is at about 20 microseconds into the frequency sweep. The voltage minimum indicates the occurrence of resonance and the detection time is consistent with the resonant frequency being 1.76 megahertz and the frequency being swept over the range 1 megahertz to about 10.6 megahertz in a time period of 240 microseconds.

FIG. 6B shows the output signals from the resonant circuit 155 (curve X) and peak detection circuit 232 (curve Y) when a capacitor value of 0.82 nanofarads is used in the resonant circuit 155. As shown in Table 1 above, this capacitance value produces a resonant frequency of 5.57 megahertz. The graph of FIG. 6B shows a voltage minimum Vmin occurring around the mid-point of curve Y, that is, at about 120 microseconds into the frequency sweep. The voltage minimum indicates the occurrence of resonance and the detection time is consistent with the resonant frequency being 5.57 megahertz and the frequency being swept over the range 1 megahertz to about 10.6 megahertz in a time period of 240 microseconds.

FIG. 6C shows the output signals from the resonant circuit 155 (curve X) and peak detection circuit 232 (curve Y) when a capacitor value of 0.27 nanofarads is used in the resonant circuit 155. As shown in Table 1 above, this capacitance value produces a resonant frequency of 9.71 megahertz. The graph of FIG. 6C shows a voltage minimum Vmin occurring relatively late in curve Y, that is, at about 220 microseconds into the frequency sweep. The voltage minimum indicates the occurrence of resonance and the detection time is consistent with the resonant frequency being 9.71 megahertz and the frequency being swept over the range 1 megahertz to about 10.6 megahertz in a time period of 240 microseconds.

Figure 7:
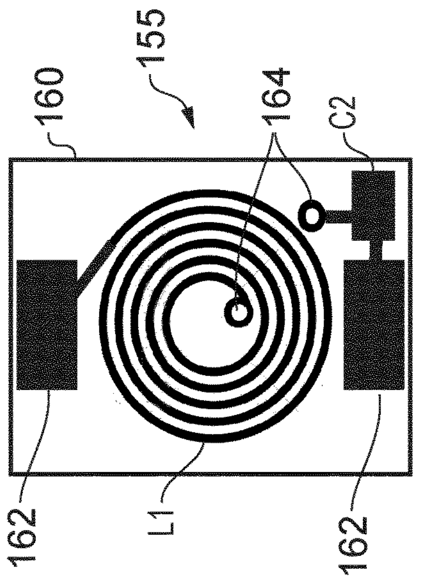
FIG. 7 is a plan view of a printed circuit board having a resonant circuit thereon.

FIG. 7 is a plan view of a printed circuit board 160 having a resonant circuit 155 arranged thereon. The resonant circuit 155 comprises an inductor L1 and a capacitor C2 connected in series. The inductor L1 is formed directly on the printed circuit board 160 as a conductive track. The inductor can be formed by any suitable method, for example, by printing an electrically conductive material on to the printed circuit board 160 or by etching a copper-clad board to form the pattern of the inductor L1. The inductor L1 comprises 15 turns (a number of turns are omitted from FIG. 7 for clarity) and the printed circuit board 160 is double-sided with half the turns being formed on one side of the printed circuit board 160 and the other half of the turns being formed on the other side. Conductive vias 164 connect the respective ends of the turns printed on each side of the printed circuit board 160. Electrically conductive contact pads 162 are formed at opposing ends of the printed circuit board 160 which can be used to connect the resonant circuit 155 in parallel across an electric heater and to an alternating signal source. One end of the inductor L1 is connected to one of the contact pads 162 and a terminal of the capacitor C2 is connected to the other contact pad 162. The dimensions of the printed circuit board 160 are 9×7×0.6 millimetres and therefore can easily fit within a cartridge or mouthpiece of an aerosol-generating system.

Figure 8:
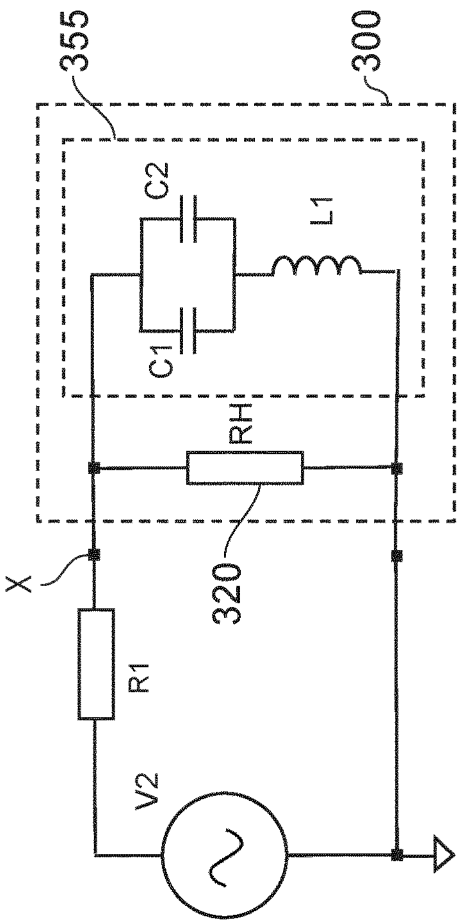
FIG. 8 shows a schematic circuit diagram of another example cartridge comprising another resonant circuit, in which the example cartridge is connected to an alternating signal source.

FIG. 8 shows a schematic circuit diagram of another example cartridge 300 comprising another resonant circuit 355. The cartridge 300 is connected to an alternating signal source V2 in order to identify the cartridge 300. The arrangement and operation of the circuit of FIG. 8 is the same as the circuit of FIG. 3B with the exception that, instead of using a single capacitor C1 in the resonant circuit 155, the resonant circuit 355 of FIG. 8 uses two capacitors C1 and C2 in parallel. The parallel arrangement of capacitors C1 and C2 helps to improve the frequency response of the resonant circuit 355.

As mentioned above, all real electronic components have parasitic elements, that is, unavoidable characteristics in addition to the intended characteristic of the component. For example, the capacitor C1 and inductor L1 in the circuit of FIG. 3B each have a parasitic resistance which is equivalent to a resistance of 0.1 ohms in series with the capacitor C1 and a resistance of 1 ohm in series with the inductor L1. These parasitic elements result in energy losses within the circuit and therefore need to be minimised.

The inventors have found that using two capacitors C1 and C2 in parallel reduces parasitic elements in the resonant circuit 355. In particular, the capacitor equivalent series resistance is reduced to 0.05 ohms. Furthermore, when capacitors are added in parallel their capacitances are summed. Therefore, by using two of the same capacitor in parallel, the inductance can be halved for the same resonant frequency. Consequently, a smaller inductor can be used which saves on printed circuit board area. The resonant circuit 355 uses an inductor having an inductance of 0.5 microhenries.

To produce the same resonant frequencies as were achieved for the circuit in FIG. 3B, the parallel arrangement of capacitors C1 and C2 in resonant circuit 355 of FIG. 8 uses two of each the capacitor values shown in Table 1 above so that the capacitance is double that shown in Table 1. The capacitance values and resulting resonant frequencies are shown in Table 2 below.

TABLE 2

| | Capacitance (nanofarads) | | | | | | | | | |
|---|---|---|---|---|---|---|---|---|---|---|
| | 16.4 | 11.2 | 7.8 | 5.4 | 3.6 | 2.4 | 1.64 | 1.12 | 0.78 | 0.54 |
| Resonant freq. (megahertz) | 1.76 | 2.13 | 2.56 | 3.07 | 3.76 | 4.61 | 5.57 | 6.74 | 8.08 | 9.71 |

As can be seen from Table 2, the parallel arrangement of two capacitors C1 and C2 achieves the same resonant frequencies as Table 1 when an inductor of 0.5 microhenries is used.

When the cartridge 300 of FIG. 8 is connected to a DC voltage source (not shown), it functions in the same way as the cartridge 100 of FIG. 3A. That is, capacitors C1 and C2 block DC voltage so that current passes only through the heater 320.

Figure 9:
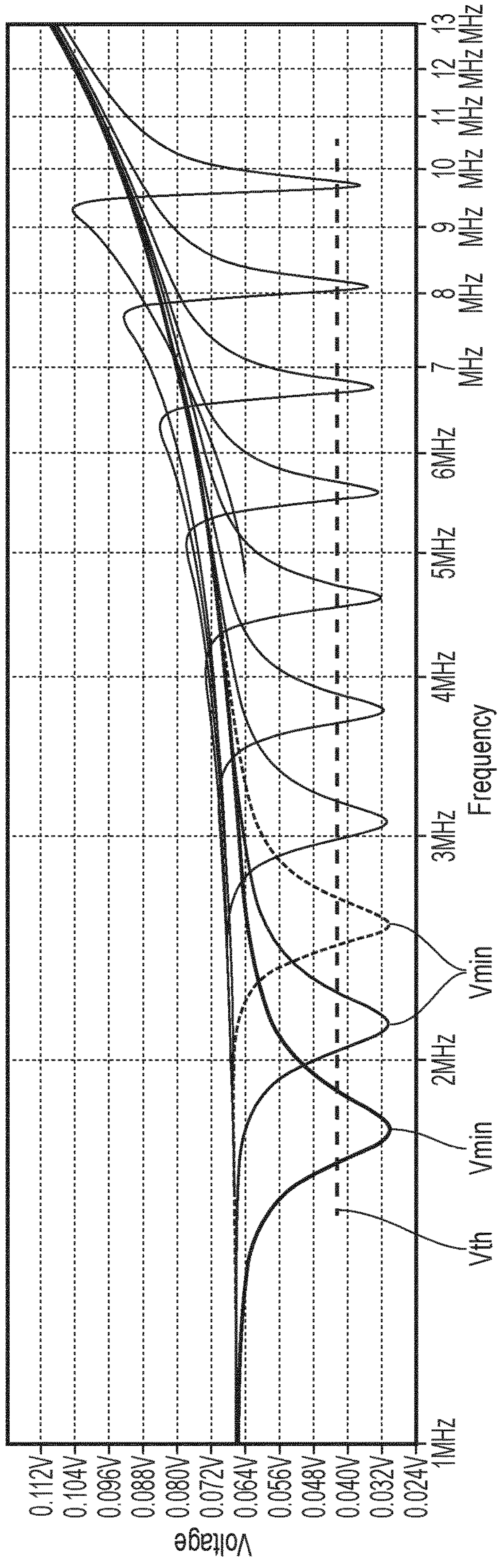
FIG. 9 is a graph of frequency versus voltage showing the frequency response of the resonant circuit of FIG. 8 when using different capacitor values.

FIG. 9 is a graph of frequency versus voltage showing the frequency response of the resonant circuit 355 of FIG. 8. In FIG. 9, there is a frequency response curve for each of the different capacitance values of Table 2. The output signal for resonant circuit 355 was measured at point X in the circuit of FIG. 8, that is, between resistor R1 and the resonant circuit 355. The graph is very similar to the graph of FIG. 4 and shows voltage minimums Vmin at the same frequencies as in FIG. 4, which correspond to the resonant frequencies of the different capacitance values in Table 2.

However, FIG. 9 shows an improved frequency response for resonant circuit 355 of FIG. 8 compared to the frequency response for the resonant circuit 155 of FIG. 3B shown in FIG. 4. That is, the magnitude of the output signal from the resonant circuit 355 is improved in resonant circuit 355 compared to resonant circuit 155. As can be seen in FIG. 9, the frequency response curves have lower voltage minimums Vmin than the frequency response curves in FIG. 4 for a particular resonant frequency.

Figure 10:
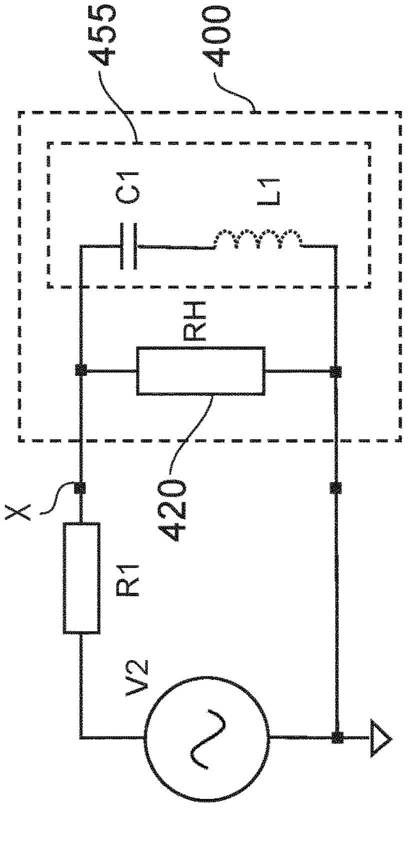
FIG. 10 shows a schematic circuit diagram of yet another example cartridge comprising a another resonant circuit, in which the example cartridge is connected to an alternating signal source.

FIG. 10 shows a schematic circuit diagram of another example cartridge 400 comprising another resonant circuit

455. The cartridge 400 is connected to an alternating signal source V2 in order to identify the cartridge 400. The arrangement and operation of the circuit of FIG. 10 is the same as the circuits of FIGS. 3B and 8 with the exception that the resonant circuit 455 does not use an inductor, in particular it does not use an actual discrete inductor component. Instead, the resonant circuit 455 uses a parasitic inductance L1 of the resonant circuit in combination with a capacitor C1 to produce resonance. The parasitic inductance L1 is denoted in FIG. 10 with a dotted line to emphasise that it is not an actual component but is instead a characteristic of the resonant circuit 455.

The parasitic inductance L1 arises as a result of the geometry of the resonant circuit 455 which forms a half-loop or half-turn when arranged in parallel with the heater 420. The half-loop generates a small parasitic inductance L1. The parasitic inductance is equivalent to an inductance of 10 nanohenries arranged in series with the capacitor C1, as shown in FIG. 10.

Parasitic inductances are relatively small compared to the inductance of actual inductor components and consequently the resonant frequencies they produce are generally higher than the previous examples. The resonant frequency is in the range 1 megahertz to 50 megahertz and to produce resonant frequencies in this range higher capacitor values are used. To produce different resonant frequencies, ten different capacitor values taken from the E12 series of capacitor values were used for capacitor C1. The C1 capacitance values and the resulting resonant frequencies are shown in Table 3 below.

TABLE 3

| | Capacitance (nanofarads) | | | | | | | | | |
|---|---|---|---|---|---|---|---|---|---|---|
| | 82 | 56 | 39 | 27 | 18 | 12 | 8.2 | 5.6 | 3.9 | 2.7 |
| Resonant freq. (megahertz) | 5.6 | 6.8 | 8.1 | 9.7 | 11.9 | 14.6 | 17.6 | 21.3 | 25.5 | 30.7 |

As can be seen from Table 3, the inventors were able to achieve ten different resonant frequencies to distinguish ten different cartridges.

When the cartridge 400 of FIG. 10 is connected to a DC voltage source (not shown), it functions in the same way as the cartridge 100 of FIG. 3A. That is, capacitor C1 blocks DC voltage so that current passes only through the heater 420.

Figure 11:
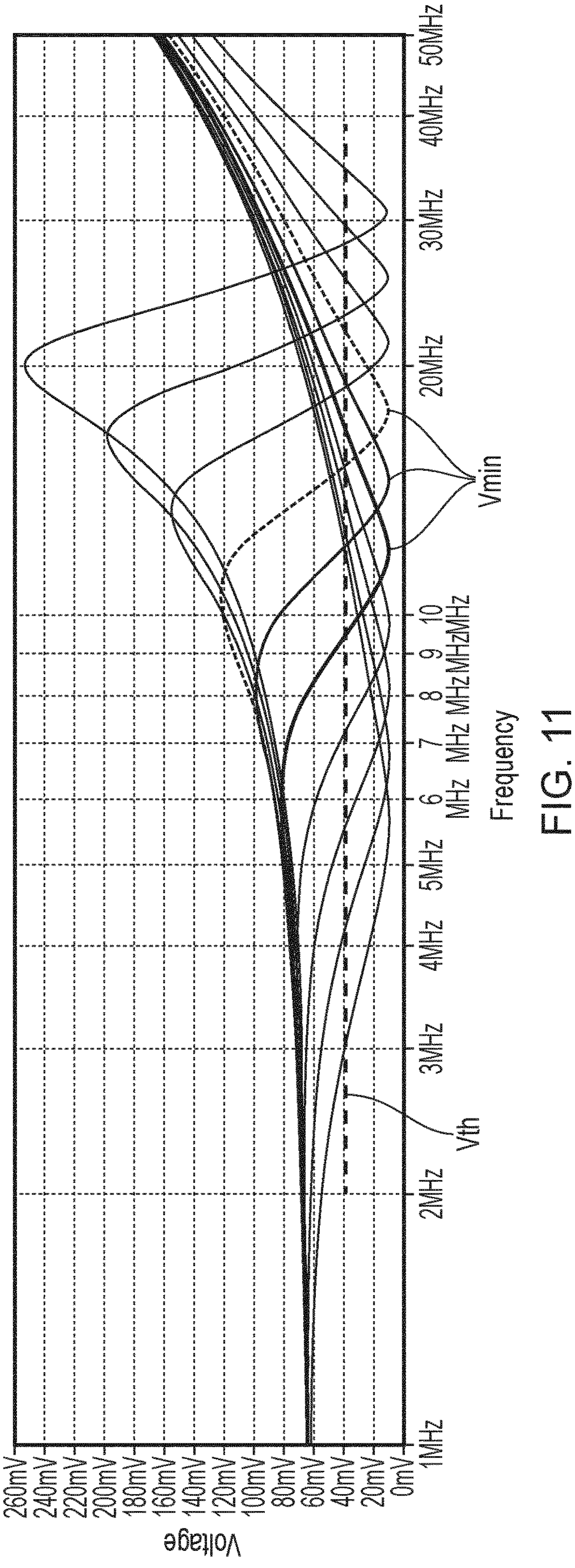
FIG. 11 is a graph of frequency versus voltage showing the frequency response of the resonant circuit of FIG. 10 when using different capacitor values.

FIG. 11 is a graph of frequency versus voltage showing the frequency response of the resonant circuit 455 of FIG. 10. In FIG. 11, there is a frequency response curve for each of the different capacitance values of Table 3. The output signal for resonant circuit 355 was measured at point X in the circuit of FIG. 10, that is, between resistor R1 and the resonant circuit 455. For each of the frequency response curves in FIG. 11, a voltage minimum Vmin can be seen occurring at each of the resonant frequencies in Table 3, which correspond to the different capacitor values used. The voltage minimums occur over a relatively small section of the entire length of the frequency response curves and are therefore easily discernible and detectable.

The minimum voltages can be detected by a peak detection circuit. The frequency at which the minimum voltage is detected provides an indication of the resonant frequency of the resonant circuit and the identity of the cartridge. Alternatively, the resonant frequency can be determined by configuring an aerosol-generating device to detect when the output signal drops below a threshold voltage Vth denoted by a horizontal dotted line in FIG. 11.

Figure 12:
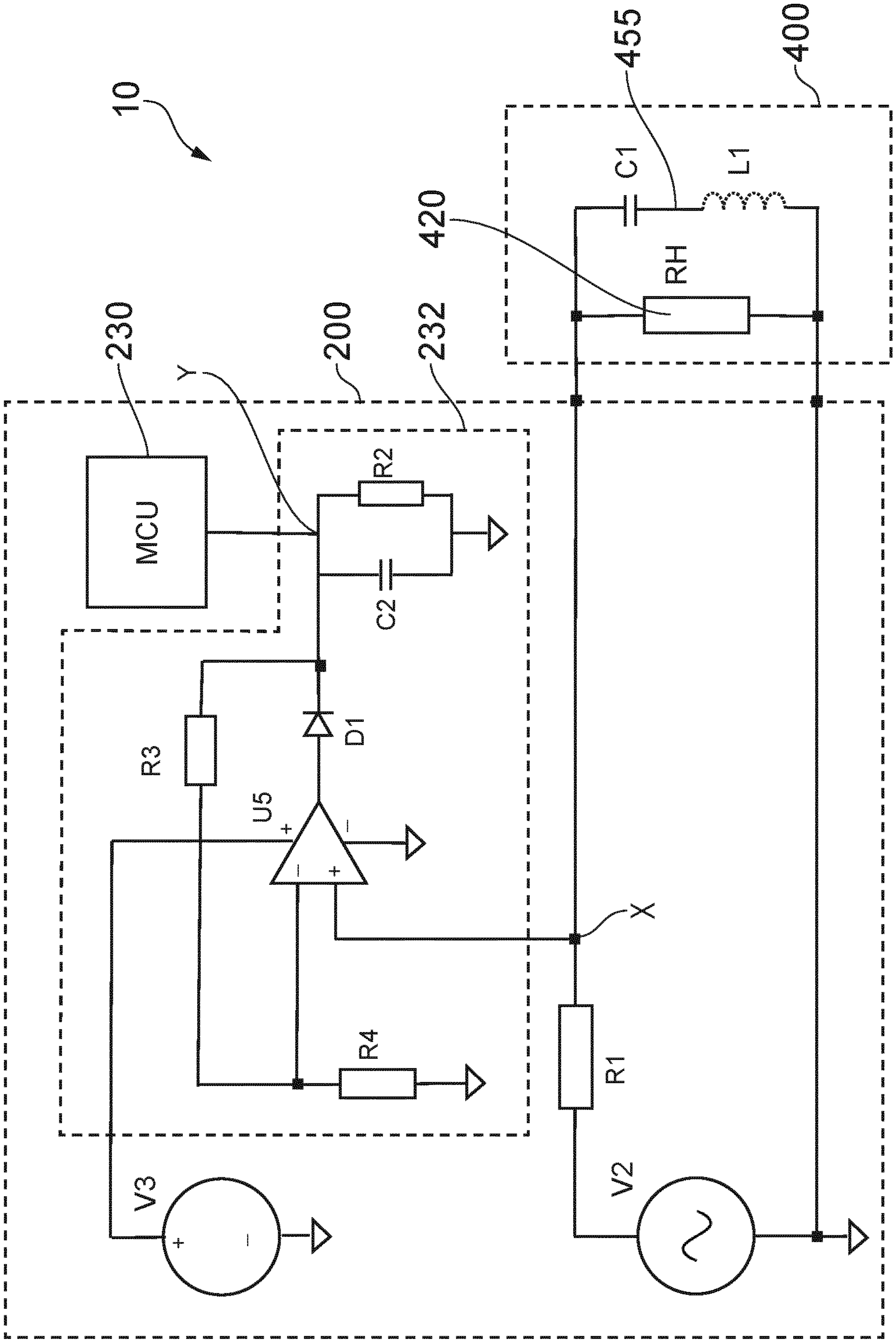
FIG. 12 is a schematic diagram of an example circuit for an aerosol-generating system for determining the resonant frequency of a resonant circuit of a cartridge. The cartridge is the example cartridge of FIG. 10.

FIG. 12 is a schematic diagram of an example circuit for an aerosol-generating system 10 for determining the resonant frequency of a resonant circuit 455 of a cartridge 400. The circuit of FIG. 12 is the same as that in FIG. 5 with the exception that the cartridge 400 is the example cartridge of FIG. 10. The lower part of the circuit of FIG. 12 shows a cartridge comprising the resonant circuit 455 and a heater 420 connected to an alternating signal source V2 in order to identify the cartridge 400. The arrangement and operation of this part of the circuit of FIG. 12 is the same as the circuit shown in FIG. 10 and, for conciseness, is not repeated here.

The circuit of FIG. 12 also comprises a peak detection circuit 232 for detecting the maximum or minimum amplitude of the output signal from the resonant circuit 455. The arrangement and operation of the peak detection circuit 232 is identical to that in FIG. 5 and therefore, for conciseness, is not repeated here.

The microcontroller 230 samples the output from the peak detection circuit over the time period taken to sweep the frequency of the alternating signal over the desired frequency range, which in this case is 1 megahertz to about 40 megahertz and takes about 1 millisecond. In this manner, the microcontroller 230 obtains a profile of the amplitude of the output signal from the resonant circuit over the range of swept frequencies. The samples are analysed by the microcontroller 230 to determine a minimum value. Since the microcontroller 230 also controls alternating signal source V2 and the frequency of the alternating signal being provided to the resonant circuit 455 of the cartridge 400, the microcontroller 230 is able to determine the frequency at which the minimum value of the output from the peak detection circuit 232 was detected. This frequency is the frequency at which resonance occurred in the resonant circuit 455 and indicates the identity of the cartridge.

Figure 13A:
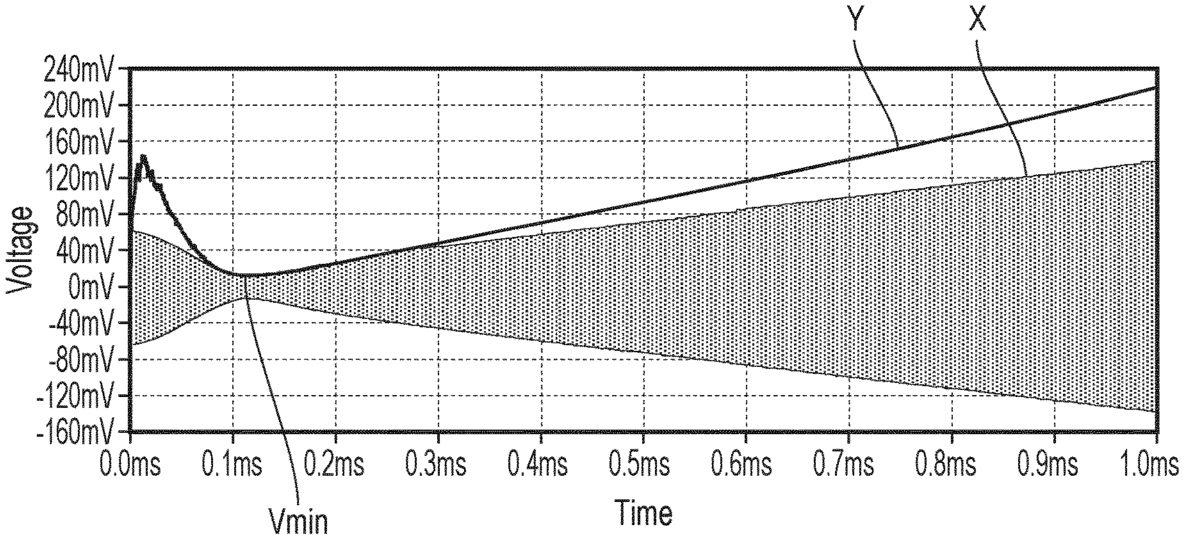
FIGS. 13A to 13C are graphs of voltage versus time showing the detection of resonance for differing values of capacitor in the resonant circuit of FIG. 10.
Figure 13B:
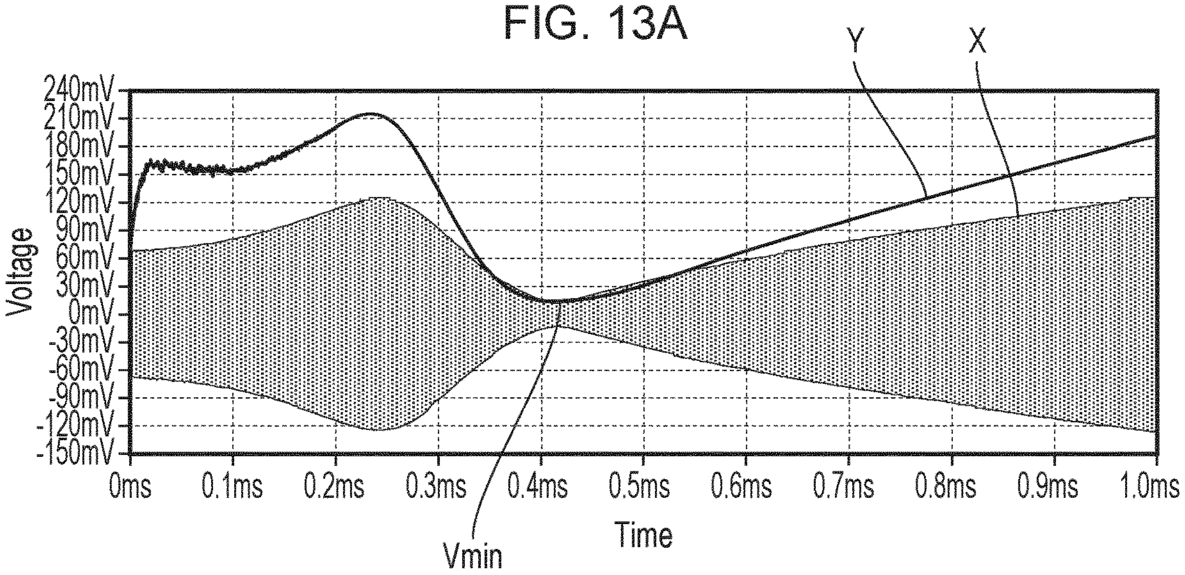
Figure 13C:
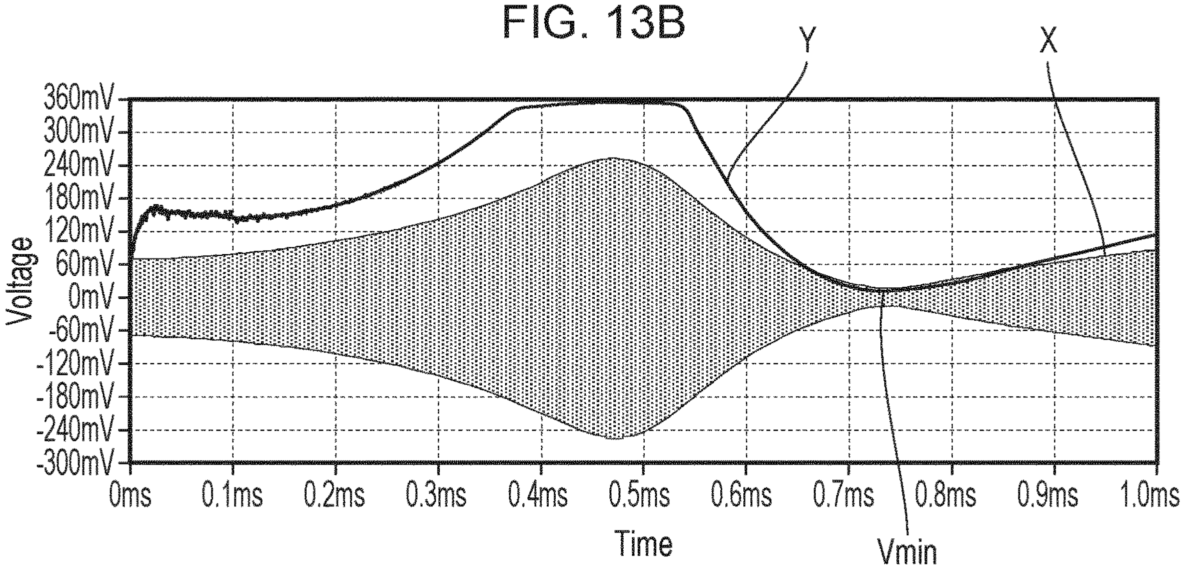

FIGS. 13A to 13C are graphs of voltage versus time showing the detection of resonance for different values of capacitor in the resonant circuit 455 in the cartridge 400 of FIG. 12. The graphs show two curves: curve X which corresponds to the output signal from the resonant circuit 455 measured at point X in the circuit of FIG. 12; and curve Y which corresponds to the output from the peak detection circuit 232 at point Y in the circuit of FIG. 12.

FIG. 12A shows the output signals from the resonant circuit 455 (curve X) and peak detection circuit 232 (curve Y) when a capacitor value of 82 nanofarads is used in the resonant circuit 455. As shown in Table 3 above, this capacitance value produces a resonant frequency of 5.6 megahertz. The graph of FIG. 12A shows a voltage minimum Vmin occurring relatively early in curve Y, that is at about 0.1 milliseconds into the frequency sweep. The voltage minimum indicates the occurrence of resonance and the detection time is consistent with the resonant frequency being 5.6 megahertz and the frequency being swept over the range 1 megahertz to about 40 megahertz in a time period of 1 milliseconds.

FIG. 12B shows the output signals from the resonant circuit 455 (curve X) and peak detection circuit 232 (curve Y) when a capacitor value of 8.2 nanofarads is used in the resonant circuit 455. As shown in Table 3 above, this capacitance value produces a resonant frequency of 17.6 megahertz. The graph of FIG. 12B shows a voltage minimum Vmin occurring around the mid-point of curve Y, that is, between about 0.4 and 0.5 milliseconds into the frequency sweep. The voltage minimum indicates the occurrence of resonance and the detection time is consistent with the resonant frequency being 17.6 megahertz and the frequency being swept over the range 1 megahertz to about 40 megahertz in a time period of 1 milliseconds.

FIG. 12C shows the output signals from the resonant circuit 455 (curve X) and peak detection circuit 232 (curve Y) when a capacitor value of 2.7 nanofarads is used in the resonant circuit 455. As shown in Table 3 above, this capacitance value produces a resonant frequency of 30.7 megahertz. The graph of FIG. 12C shows a voltage minimum Vmin occurring relatively late in curve Y, that is, between 0.7 and 0.8 milliseconds into the frequency sweep. The voltage minimum indicates the occurrence of resonance and the detection time is consistent with the resonant frequency being 30.7 megahertz and the frequency being swept over the range 1 megahertz to about 40 megahertz in a time period of 1 milliseconds.

For the purpose of the present description and of the appended claims, except where otherwise indicated, all numbers expressing amounts, quantities, percentages, and so forth, are to be understood as being modified in all instances by the term “about”. Also, all ranges include the maximum and minimum points disclosed and include any intermediate ranges therein, which may or may not be specifically enumerated herein. In this context, therefore, a number A is understood as A±5 percent of A. Within this context, a number A may be considered to include numerical values that are within general standard error for the measurement of the property that the number A modifies. The number A, in some instances as used in the appended claims, may deviate by the percentages enumerated above provided that the amount by which A deviates does not materially affect the basic and novel characteristic(s) of the claimed invention. Also, all ranges include the maximum and minimum points disclosed and include any intermediate ranges therein, which may or may not be specifically enumerated herein.

The invention claimed is:

1. A cartridge for an aerosol-generating device, the cartridge comprising:

an aerosol-forming substrate;

an electric heater configured to heat the aerosol-forming substrate, the electric heater being a resistive heater configured to be heated by a direct current (DC) voltage; and a resonant circuit comprising a capacitor and an inductor connected in series, the resonant circuit being connected in parallel with the electric heater, wherein the resonant circuit is configured to resonate at a predetermined resonant frequency, and wherein the predetermined resonant frequency is associated with an identity of the cartridge.

2. The cartridge according to claim 1, wherein the predetermined resonant frequency of the resonant circuit is determined by a capacitance of the capacitor, and wherein the predetermined resonant frequency can be changed by changing the capacitance of the capacitor.

3. The cartridge according to claim 1, wherein the predetermined resonant frequency is in a range of 10 kHz to 100 MHz.

4. The cartridge according to claim 1, wherein the predetermined resonant frequency is in a range of 1 MHz to 11 MHz.

5. The cartridge according to claim 1, wherein a capacitance of the capacitor is in a range of 0.1 nF to 10 nF.

6. The cartridge according to claim 1, wherein the resonant circuit further comprises a plurality of capacitors arranged in parallel, and wherein a combined capacitance of the plurality of capacitors is used to produce resonance.

7. The cartridge according to claim 1, wherein the resonant circuit is arranged on a printed circuit-board (PCB), and wherein the inductor is formed directly on the PCB as a conductive track.

8. The cartridge according to claim 1, wherein the resonant circuit is arranged to be connected to an alternating signal source and is configured to resonate when the predetermined resonant frequency substantially equals a frequency of the alternating signal.

9. An aerosol-generating device, comprising:

a housing configured to receive a cartridge according to claim 1, wherein the housing comprises an electrical connection configured to electrically connect to the cartridge;

a power source configured to supply electrical power to the electric heater of the cartridge;

an alternating signal source configured to input an alternating signal to the resonant circuit of the cartridge; and control circuitry configured to control a supply of electrical power to the electric heater and to controllably vary a frequency of the alternating signal supplied to the resonant circuit, wherein the control circuitry is arranged to receive an output signal from the resonant circuit, and wherein the control circuitry is further configured to:

determine when resonance occurs in the resonant circuit by detecting when the output signal reaches a predetermined threshold value, determine a frequency at which resonance occurs, and identify the cartridge based on the determined resonant frequency.

10. The aerosol-generating device according to claim 9, wherein the control circuitry is further configured to sweep the frequency of the alternating signal over a predetermined frequency range within a predetermined time period, and wherein the predetermined time period is 5 milliseconds or less.

11. The aerosol-generating device according to claim 9, wherein a peak voltage of the alternating signal supplied to the resonant circuit is 2 V or less.

12. The aerosol-generating device according to claim 9, wherein a peak voltage of the alternating signal supplied to the resonant circuit is 1 V or less.

13. An aerosol-generating system, comprising:

a cartridge comprising:

an aerosol-forming substrate, an electric heater configured to heat the aerosol-forming substrate, the electric heater being a resistive heater configured to be heated by a direct current (DC) voltage, and a resonant circuit comprising a capacitor and an inductor connected in series, the resonant circuit being connected in parallel with the electric heater and being configured to resonate at a predetermined resonant frequency, the predetermined resonant frequency being associated with an identity of the cartridge; and an aerosol-generating device comprising:

a housing configured to receive the cartridge, wherein the housing comprises an electrical connection configured to electrically connect to the cartridge, a power source configured to supply electrical power to the electric heater of the cartridge, an alternating signal source configured to input an alternating signal to the resonant circuit of the cartridge, and control circuitry configured to control a supply of electrical power to the electric heater and to controllably vary a frequency of the alternating signal supplied to the resonant circuit, wherein the control circuitry is arranged to receive an output signal from the resonant circuit, and wherein the control circuitry is further configured to:

determine when resonance occurs in the resonant circuit by detecting when the output signal reaches a predetermined threshold value, determine a frequency at which resonance occurs, and identify the cartridge based on the determined resonant frequency.

* * * * *